(12) United States Patent
Waaler et al.

(10) Patent No.: US 9,326,812 B2
(45) Date of Patent: May 3, 2016

(54) PORTABLE SURGICAL INSTRUMENT

(75) Inventors: Luke Waaler, Longmont, CO (US); Duane E. Kerr, Loveland, CO (US); Diana Gunnarson, Longmont, CO (US); Robert B. Stoddard, Steamboat Springs, CO (US); Sean T. O'Neill, Campbell, CA (US); Steven E. Butcher, Berthoud, CO (US); William E. Robinson, Boulder, CO (US); Cody C. Taylor, Boulder, CO (US)

(73) Assignee: Covidien LP, Mansfield, MA (US)

( * ) Notice: Subject to any disclaimer, the term of this patent is extended or adjusted under 35 U.S.C. 154(b) by 751 days.

(21) Appl. No.: 13/358,049

(22) Filed: Jan. 25, 2012

(65) Prior Publication Data

US 2013/0190759 A1 Jul. 25, 2013

(51) Int. Cl.
| | | |
|---|---|---|
| *A61B 18/14* | (2006.01) | |
| *A61B 17/32* | (2006.01) | |
| *H01M 2/10* | (2006.01) | |
| *A61B 17/00* | (2006.01) | |
| *A61B 18/12* | (2006.01) | |

(52) U.S. Cl.
CPC ..... *A61B 18/1442* (2013.01); *A61B 17/320092* (2013.01); *H01M 2/1066* (2013.01); *A61B 2017/00734* (2013.01); *A61B 2018/1226* (2013.01); *H01M 2220/30* (2013.01)

(58) Field of Classification Search
CPC ........... H01M 2/1066; H01M 2220/30; A61B 2018/1226; A61B 2017/00734
See application file for complete search history.

(56) References Cited

U.S. PATENT DOCUMENTS

| | | | |
|---|---|---|---|
| 4,722,339 A | 2/1988 | Dreier et al. | |
| 5,322,055 A | 6/1994 | Davison et al. | |
| 5,553,675 A | 9/1996 | Pitzen et al. | |
| 5,620,242 A | 4/1997 | Leon et al. | |
| 7,501,198 B2 * | 3/2009 | Barlev et al. | 429/97 |
| 8,122,632 B2 | 2/2012 | Bentley | |

(Continued)

FOREIGN PATENT DOCUMENTS

| | | |
|---|---|---|
| AU | 2011213852 A1 | 3/2012 |
| DE | 200 03 700 | 5/2000 |

(Continued)

OTHER PUBLICATIONS

Extended European Search Report corresponding to EP No. 13 15 1827.6, completed Mar. 27, 2013, and mailed Apr. 8, 2103 (7 pp).

(Continued)

*Primary Examiner* — Michael Kahelin

(57) ABSTRACT

A surgical instrument is provided and includes a housing including an elongated shaft. The housing includes a docking portion that includes one or more apertures defined therein and electrical circuitry disposed therein. An end effector is operably supported at a distal end of the elongated shaft. A battery assembly is selectively and pivotably engageable with the docking portion of the housing and configured to generate electrical energy. The battery assembly includes one or more protrusions that are configured to releasably engage the aperture(s) on the docking portion and a latch mechanism that is movable from an initial position for latching the battery assembly to the docking portion to a subsequent position for unlatching the battery assembly from the docking portion. The battery assembly is adapted to communicate with the electrical circuitry of the docking member upon insertion of the battery assembly into the at least one aperture.

14 Claims, 18 Drawing Sheets

(56) References Cited

U.S. PATENT DOCUMENTS

| | | | |
|---|---|---|---|
| 8,419,757 B2 | 4/2013 | Smith et al. | |
| 2003/0149424 A1 | 8/2003 | Barlev et al. | |
| 2005/0221654 A1* | 10/2005 | Phillips et al. | 439/347 |
| 2009/0143805 A1 | 6/2009 | Palmer et al. | |
| 2009/0240245 A1 | 9/2009 | Deville et al. | |
| 2010/0004669 A1 | 1/2010 | Smith et al. | |
| 2010/0026609 A1* | 2/2010 | Otsuki et al. | 345/8 |
| 2011/0009890 A1 | 1/2011 | Palmer et al. | |
| 2011/0257650 A1 | 10/2011 | Deville et al. | |
| 2012/0013293 A1 | 1/2012 | Chu | |
| 2012/0078278 A1 | 3/2012 | Bales, Jr. et al. | |

FOREIGN PATENT DOCUMENTS

| | | |
|---|---|---|
| JP | 06-005105 | 1/1994 |
| JP | 2000-271143 A | 10/2000 |
| JP | 2006-245347 A | 9/2006 |
| JP | 2009-508408 A | 2/2009 |
| JP | 05-284401 B2 | 9/2013 |
| WO | WO 94/24708 | 10/1994 |

OTHER PUBLICATIONS

Japan Office Action No. 2013-006046, dated Jan. 10, 2014.
Japan Office Action No. 2013-006046, dated Oct. 4, 2014.
Canada Office Action No. 2,799,129, dated Jan. 10, 2014.
Australia Office Action No. 2012268925, dated Apr. 18, 2013.
Japanese Office Action for Application No. 2014-236211 dated Oct. 1, 2015.

* cited by examiner

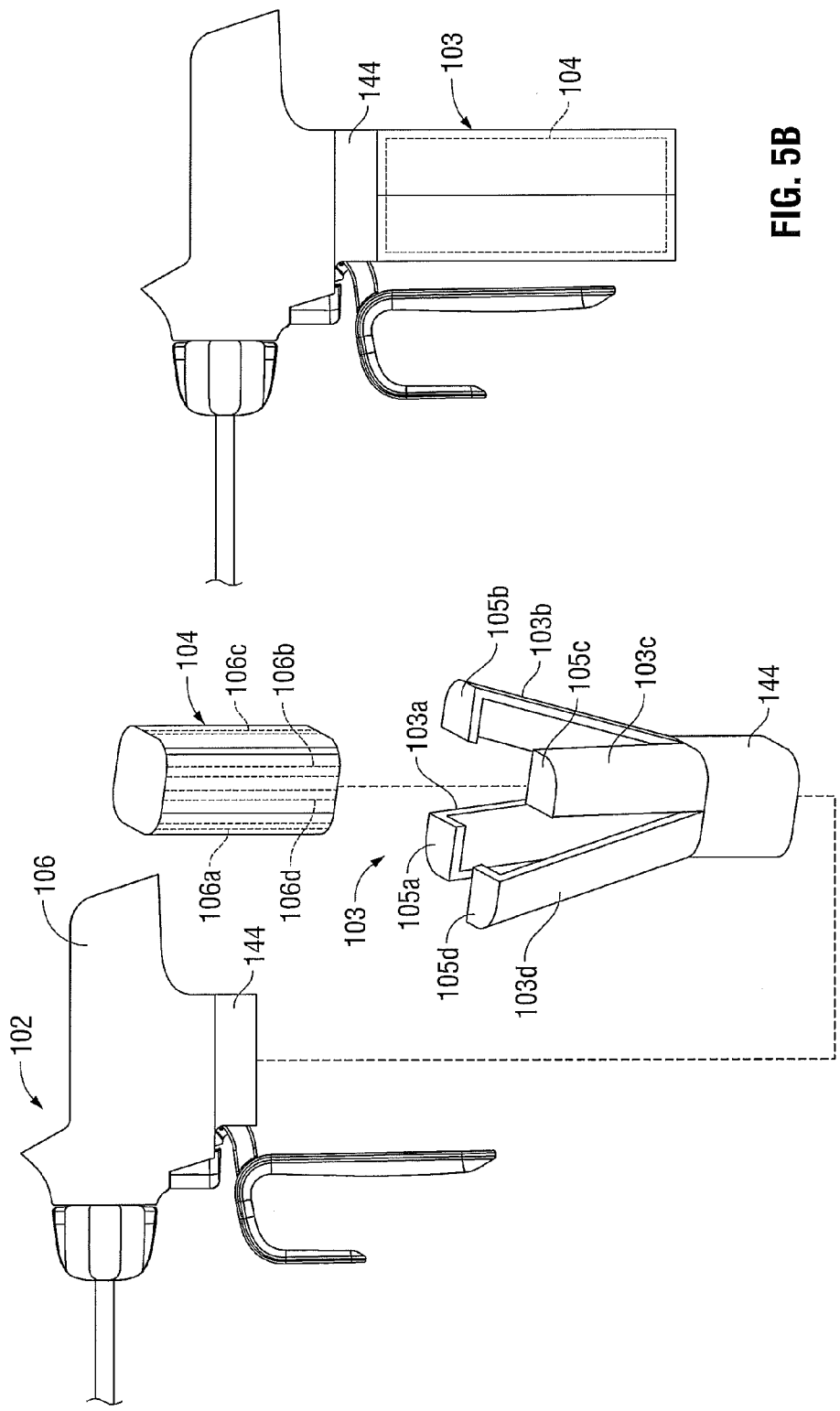

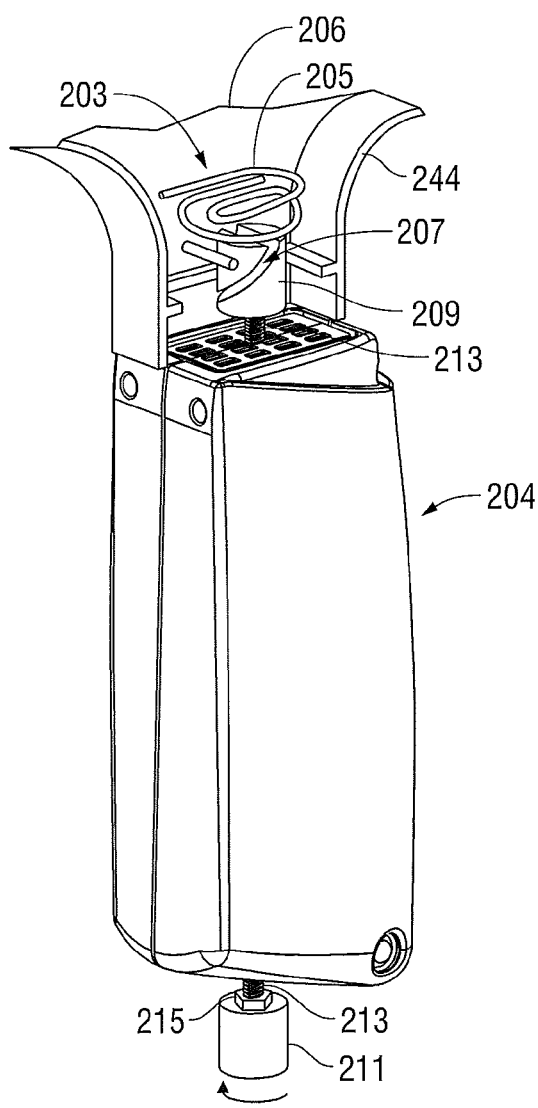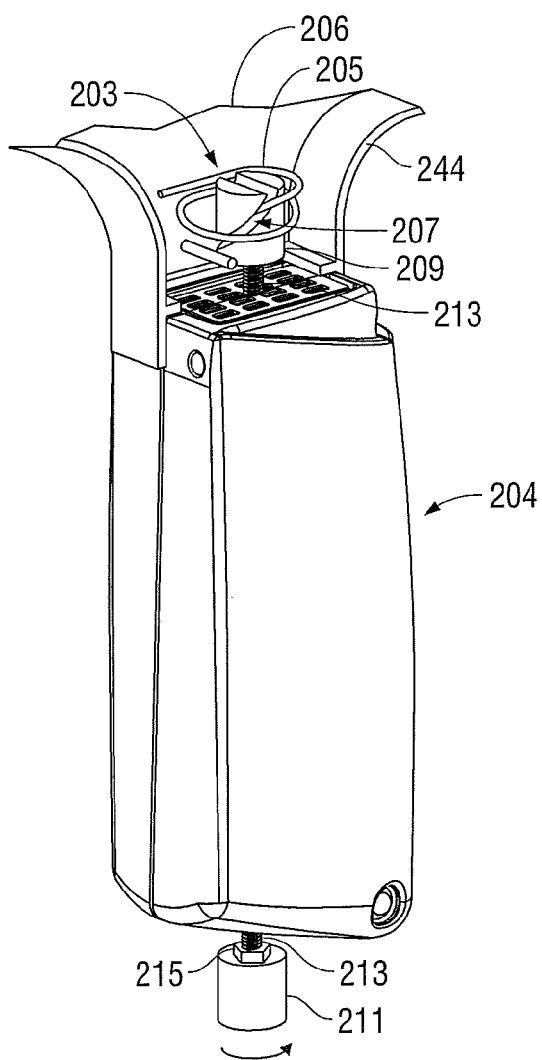
FIG. 6B
FIG. 6C

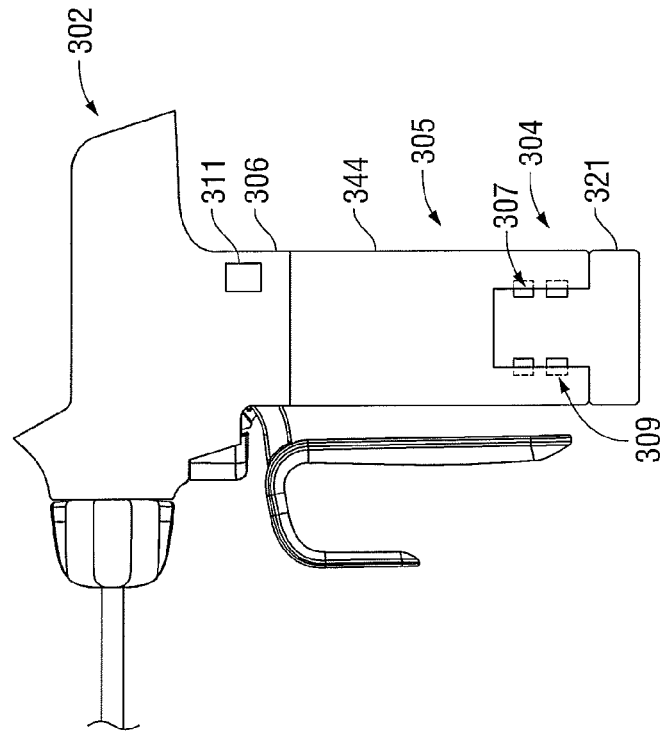
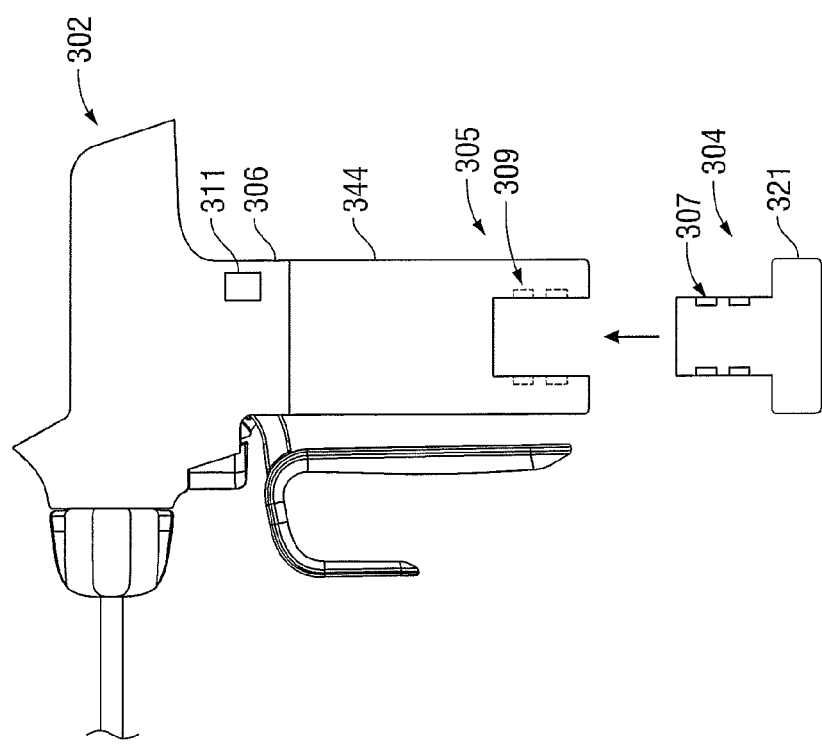
FIG. 7B
FIG. 7A

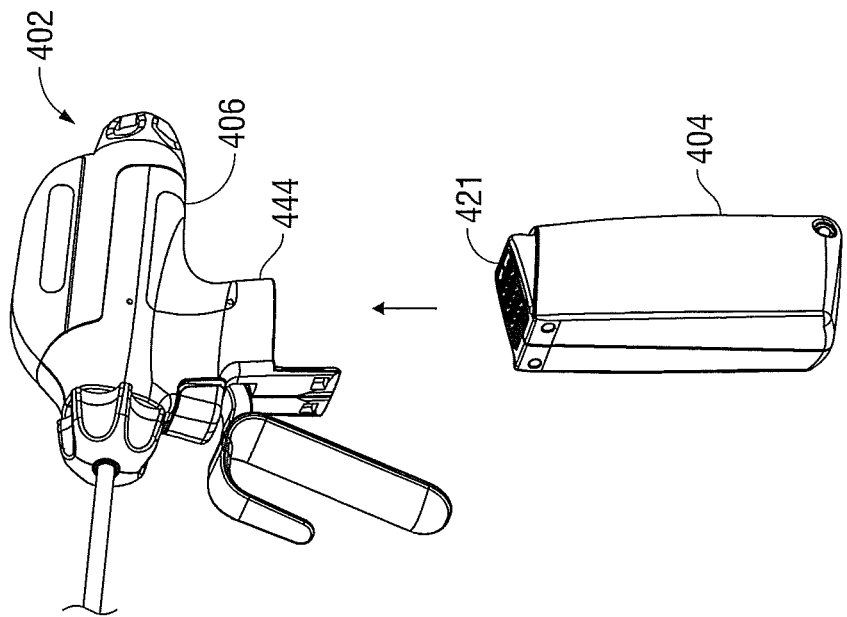
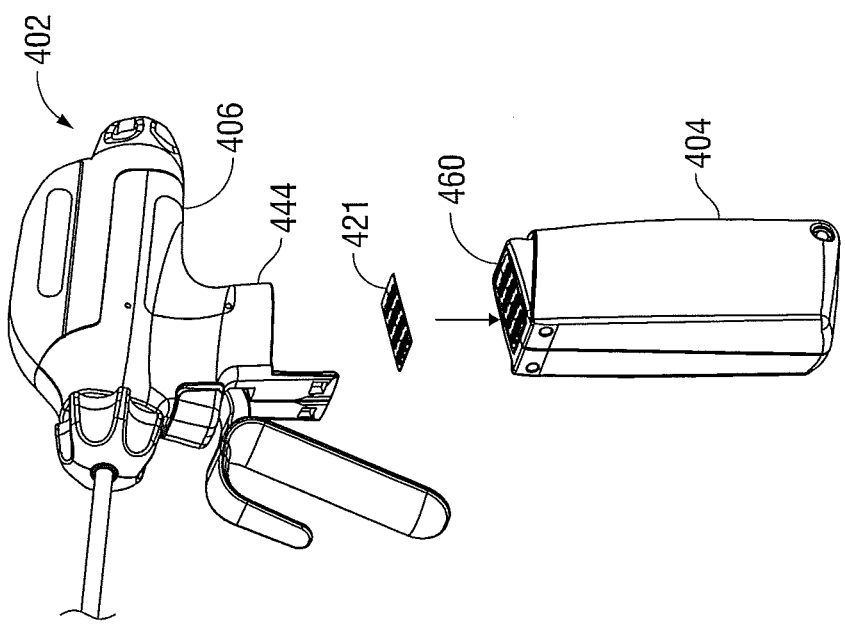
FIG. 8A
FIG. 8B

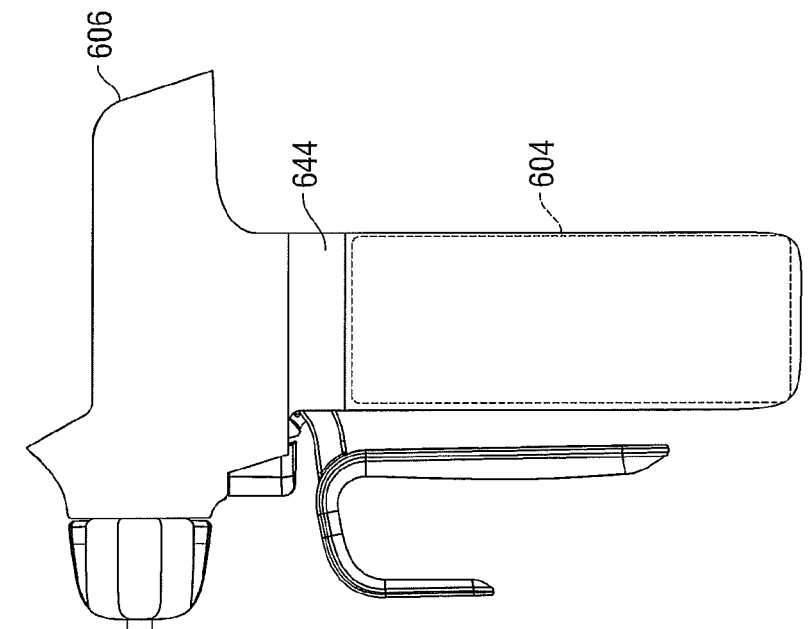
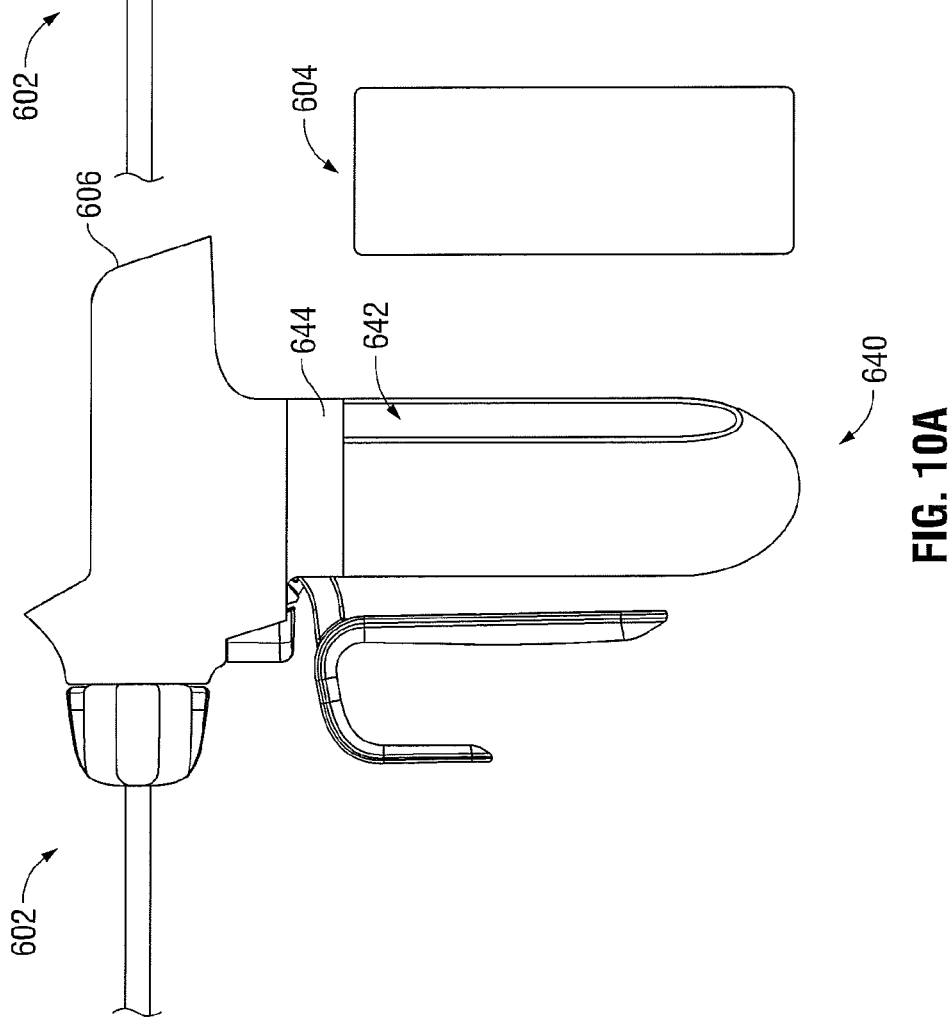
FIG. 10B
FIG. 10A

PORTABLE SURGICAL INSTRUMENT

BACKGROUND

1. Technical Field

The present disclosure relates to portable surgical instruments and, more particularly, to portable surgical instruments that utilize a handpiece configured to house a battery and/or battery assembly and releasably couple to the portable surgical instrument.

2. Background of Related Art

Portable surgical instruments are known in the medical arts. Portable surgical instruments overcome some of the drawbacks that are typically associated with surgical instruments that draw power from electrical outlets. That is, outlet driven surgical instruments utilize power cords that may create tripping and/or entanglement hazards in an operating room environment.

Typically, the portable surgical instrument includes a battery or battery assembly that is configured to removably couple or "latch" to the portable surgical instrument. In an ideal scenario, the battery or battery assembly remains coupled or "latched" to the portable surgical instrument during the entirety of the surgical procedure. Unfortunately, and in certain instances, the battery or battery assembly sometimes has to be uncoupled or "unlatched" from the portable surgical instrument during the surgical procedure. For example, the battery or battery assembly may have to be unlatched from the surgical instrument for sterilization (or re-sterilization), charging (or recharging), etc.

SUMMARY

As can be appreciated, removable batteries or battery assemblies that are configured to quickly and easily couple or latch to a handpiece of the portable surgical instrument may prove advantageous in the surgical environment.

As it is used herein, "electrosurgical procedure" generally refers to any electrosurgical procedure involving any form of energy, such as, for example, microwave energy, radiofrequency (RF) energy, ultrasonic energy, thermal energy, etc. As it is used herein, "end effector" generally refers to an end effector that is capable of treating tissue, such as, for example, end effectors that include jaw members configured to treat tissue utilizing ultrasonic energy, electrosurgical energy (e.g., radio frequency energy and/or microwave energy), and/or thermal energy; and electrosurgical stapler end effectors, e.g., anvil/cartridge assemblies, that are configured to staple and, subsequently, electrosurgically treat tissue utilizing one of the aforementioned energies.

An aspect of the present disclosure provides a surgical instrument. The surgical instrument includes a housing that includes an elongated shaft extending distally therefrom having a longitudinal axis defined therethrough. The housing includes a docking portion including one or more apertures defined therein and electrical circuitry disposed therein. An end effector is operably supported at a distal end of the elongated shaft. A battery assembly selectively and pivotably engageable to the docking portion of the housing is configured to generate electrical energy. The battery assembly includes one or more protrusions that are configured to releasably engage the aperture(s) on the docking portion and a latch mechanism that is movable from an initial position for latching the battery assembly to the docking portion to a subsequent position for unlatching the battery assembly from the docking portion. The battery assembly may be adapted to communicate with the electrical circuitry of the docking member upon insertion of the battery assembly into the at least one aperture defined in the docking portion.

A selectively removable generator may be in operative communication with the battery assembly via the electrical circuitry of the docking member.

The battery assembly may include a pivot member that is configured to pivot about a corresponding member disposed on the housing of the ultrasonic surgical instrument. In this instance, the pivot member may include a generally hook shape and may be disposed at a proximal end of the battery assembly.

The corresponding protrusions disposed on the battery assembly may be located at a distal end thereof.

In certain instance, the aperture(s) on the docking portion is further defined by two or more apertures and the protrusion(s) on the battery assembly is further defined by two or more protrusions that are configured to engage the at least two apertures.

The latch may be normally held in a retracted position by an elongated member of the docking portion. Moreover, a top portion of the latch may include a lateral bar portion that is configured to contact the protrusion(s) on the battery assembly to prevent movement of the latch past a predetermined point. Further, the latch may include a bottom portion that is ergonomically configured to receive a finger of a user.

In certain instances, the battery assembly may include an over pressure safety vent.

The end effector may include a clamping jaw member that is movable in relation to an active jaw member between an open position spaced from an operating surface of the active jaw member and a closed position in juxtaposed alignment with the operating surface of the active jaw member. Moreover, the housing may include a jaw lever for imparting movement of the clamping jaw. Further, the operating surface may be configured to one of transect, dissect, seal and coagulate tissue.

An aspect of the present disclosure provides a surgical system for treating tissue. The surgical instrument includes a housing that includes an elongated shaft extending distally therefrom having a longitudinal axis defined therethrough. The housing includes a docking portion including one or more apertures defined therein and electrical circuitry disposed therein. An end effector is operably supported at a distal end of the elongated shaft. A battery assembly selectively and pivotably engageable to the docking portion of the housing is configured to generate electrical energy. The battery assembly includes one or more protrusions that are configured to releasably engage the aperture(s) on the docking portion and a latch mechanism that is movable from an initial position for latching the battery assembly to the docking portion to a subsequent position for unlatching the battery assembly from the docking portion. A selectively removable generator is in operative communication with the battery assembly via the electrical circuitry of the docking member.

The battery assembly may include a pivot member that is configured to pivot about a corresponding member disposed on the housing of the ultrasonic surgical instrument. In this instance, the pivot member may include a generally hook shape and may be disposed at a proximal end of the battery assembly.

The corresponding protrusions disposed on the battery assembly may be located at a distal end thereof.

In certain instance, the aperture(s) on the docking portion is further defined by two or more apertures and the protrusion(s) on the battery assembly is further defined by two or more protrusions that are configured to engage the at least two apertures.

The latch may be normally held in a retracted position by an elongated member of the docking portion. Moreover, a top portion of the latch may include a lateral bar portion that is configured to contact the protrusion(s) on the battery assembly to prevent movement of the latch past a predetermined point.

An aspect of the present disclosure also provides a method of providing electrical energy to a surgical instrument. A surgical instrument that includes a housing including a docking portion having one or more apertures defined therein and electrical circuitry disposed therein is provided. A battery assembly is pivotably engaged into the at least one aperture defined in the docking portion of the surgical instrument. The battery assembly includes one or more protrusions that releasably engage the aperture(s) on the docking portion and a latch mechanism that is movable from an initial position for latching the battery assembly to the docking portion to a subsequent position for unlatching the battery assembly from the docking portion. The battery assembly is caused to communicate with the electrical circuitry of the docking member upon pivotable engagement of the battery assembly into the at least one aperture defined in the docking portion.

BRIEF DESCRIPTION OF THE DRAWINGS

Embodiments of the presently disclosed specimen retrieval apparatus are described hereinbelow with reference to the drawings wherein:

FIGS. 5A and 5B are schematic views of a battery powered surgical instrument configured for use with a removable battery assembly according to another embodiment of the present disclosure;

FIGS. 6A-6C are schematic views of a battery powered surgical instrument configured for use with a removable battery assembly according to yet another embodiment of the present disclosure;

FIGS. 7A-7B are schematic views of a battery powered surgical instrument configured for use with a removable battery assembly according to still another embodiment of the present disclosure;

FIGS. 8A and 8B are schematic views of a battery powered surgical instrument configured for use with a removable battery assembly according to still another embodiment of the present disclosure;

FIGS. 10A-10B are schematic views of a battery powered surgical instrument configured for use with a removable battery assembly according to still another embodiment of the present disclosure;

DETAILED DESCRIPTION OF THE EMBODIMENTS

Figure 1:
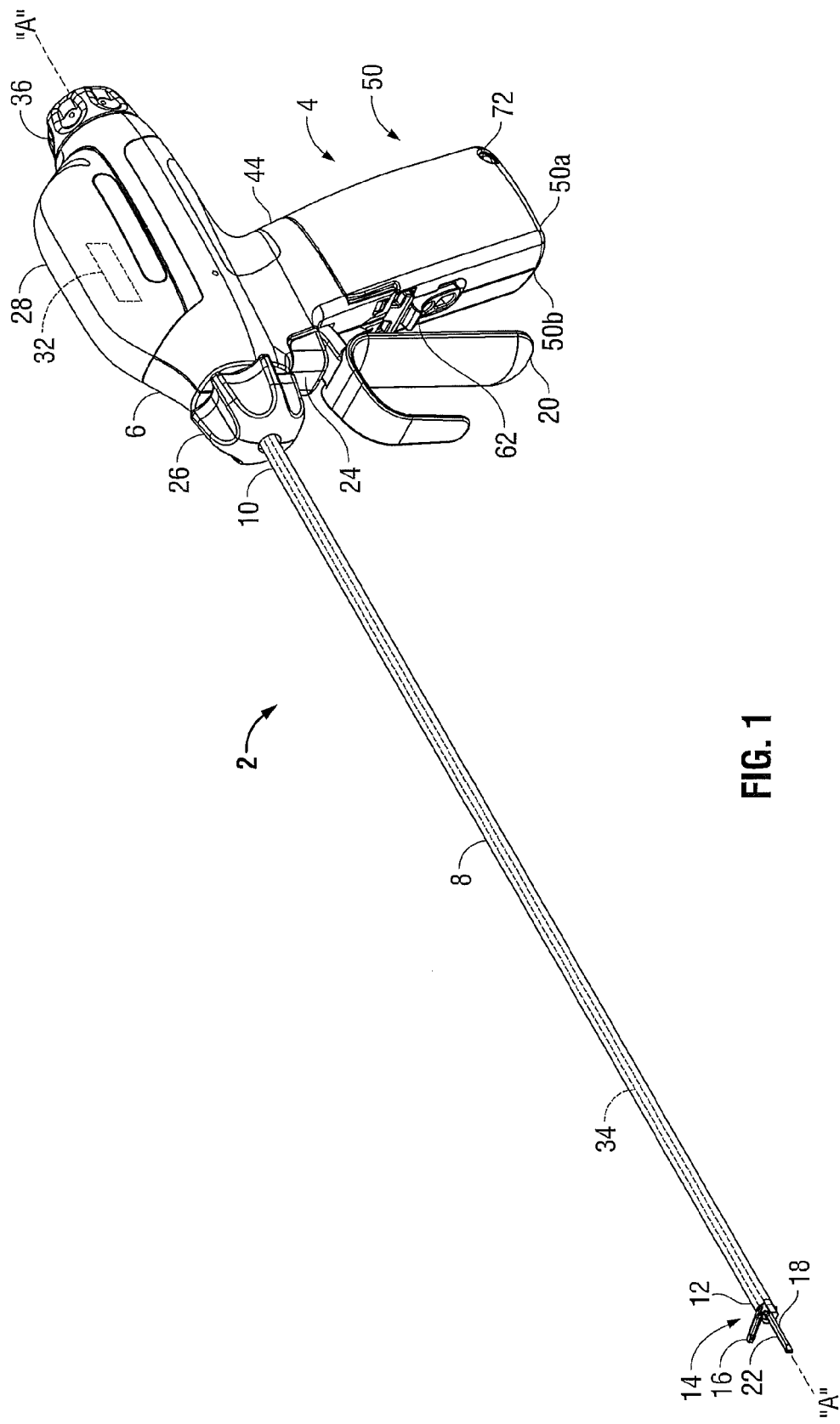
FIG. 1 is a side, perspective view of a battery powered surgical instrument configured for use with a removable battery assembly according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

With reference to FIGS. 1-4, and initially with reference to FIG. 1, a battery powered surgical instrument 2 configured for use with a removable battery assembly 4 according to an embodiment of the present disclosure is illustrated. Battery assembly 4 may be configured for use with a variety of battery powered instruments including, but not limited to, electrosurgical forceps, staplers, etc. For illustrative purposes, the battery assembly 4 is described in terms of use with a portable ultrasonic surgical instrument 2 (instrument 2).

Instrument 2 includes a housing 6 (FIGS. 1, 2A, 3 and 4) configured to house one or more components, e.g., transducer, generator and electrical circuitry that is configured for electrical communication with the battery assembly 4 of the instrument 2. A proximal end of housing 6 is configured to releasably couple to an ultrasonic generator 28 (generator 28) and the battery assembly 4, described in greater detail below. A distal end of the housing 6 is configured to support and/or couple to a shaft 8.

Shaft 8 extends from housing 6 and defines a longitudinal axis "A-A" therethrough (FIG. 1). A shaft rotation knob 26 (FIG. 1) is operably coupled to the shaft 8 and is configured to rotate the shaft 8 in either direction about the longitudinal axis "A-A." A proximal end 10 of the shaft 8 is operably coupled to the housing 6 and a distal end 12 of the shaft 8 is operably coupled to an end effector 14. The operation of parts of the end effector 14 (e.g., jaw members 16 and 18) are movable relative to one another upon actuation of handle 20 coupled to housing 6 as described in more detail below.

As can be appreciated, the configuration of the end effector 14 may be altered to accommodate a specific electrosurgical procedure. For example, if tissue is to be stapled, the end effector may include an anvil and cartridge assembly; and if tissue is to be sealed, the end effector may include a pair of jaw members that are configured to grasp and subsequently seal tissue. In the latter instance, one or more suitable energy forms may be utilized to seal the tissue, such as, for example, radio frequency energy, ultrasonic energy, etc.

Figure 2A:
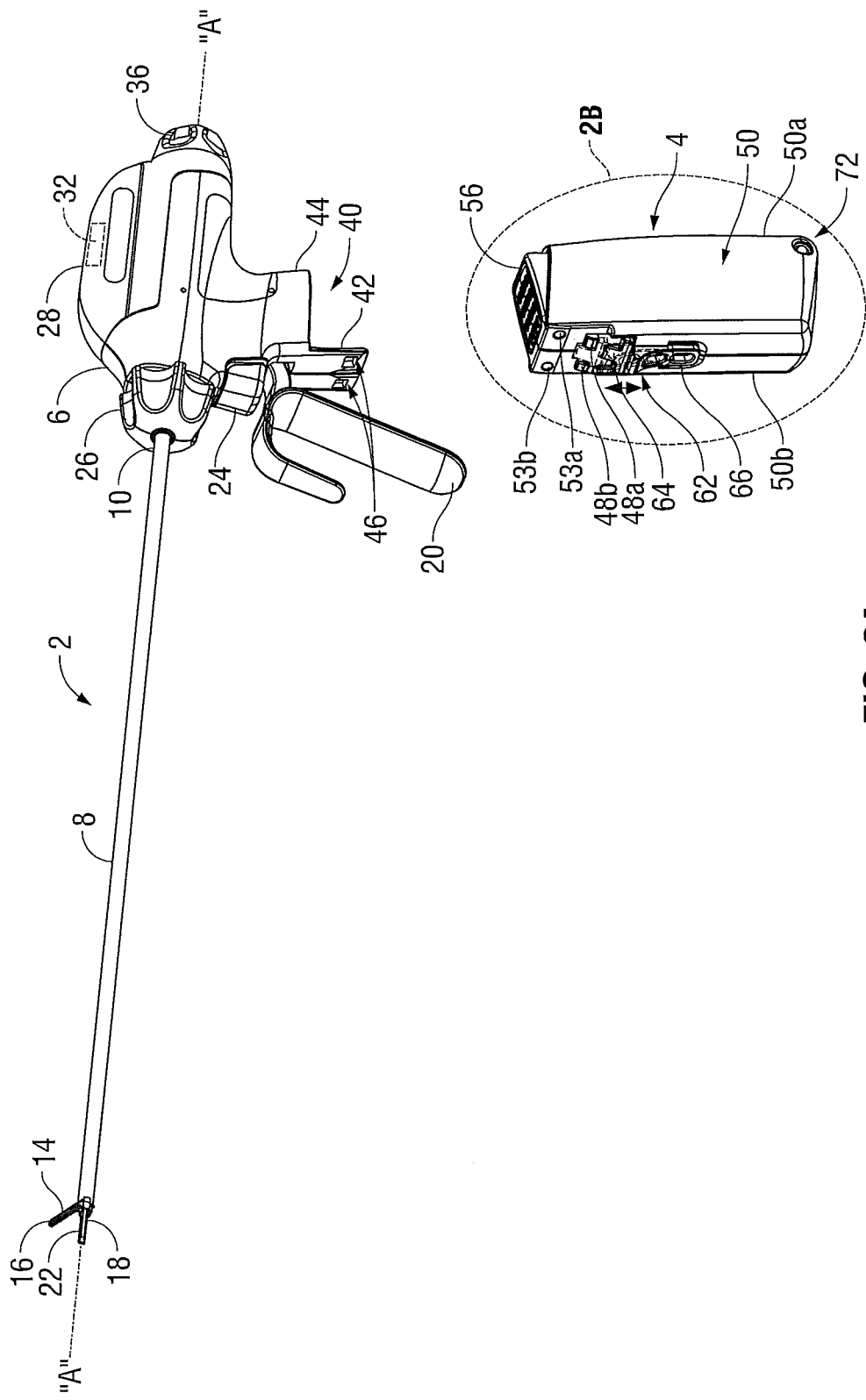
FIG. 2A is a side, perspective view of the battery powered surgical instrument depicted in FIG. 1 separated from the battery assembly.
Figure 3:
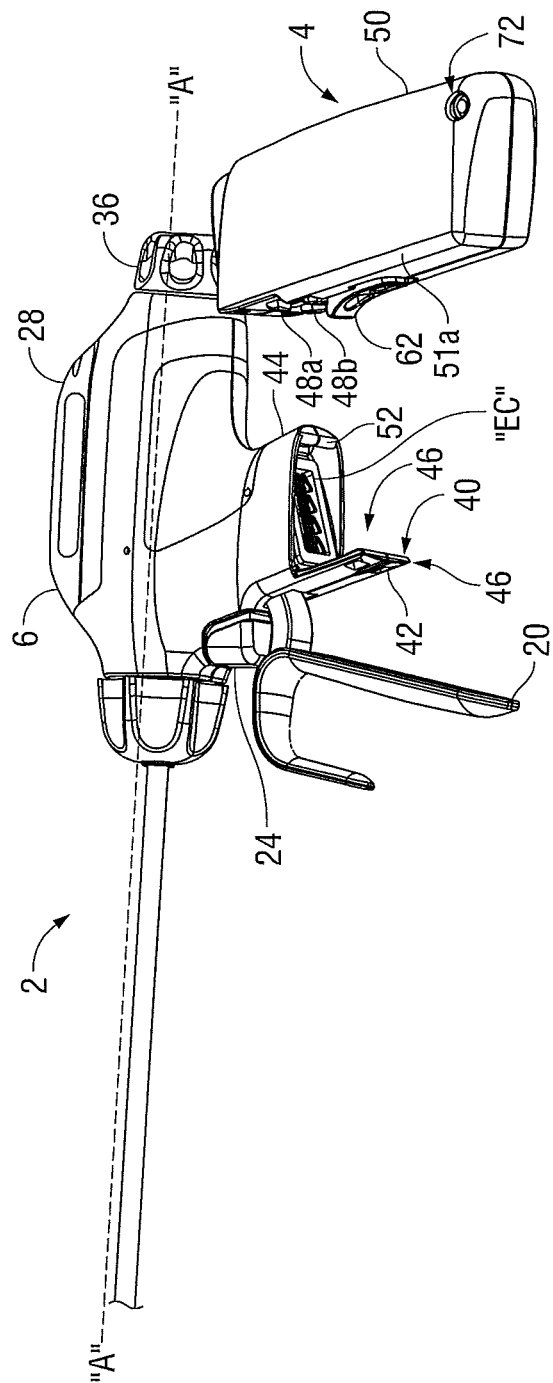
FIG. 3 is a side view of the battery powered surgical instrument depicted in FIG. 1 separated from the battery assembly and rotated about a longitudinal axis "A-A"

End effector 14 includes a pair of jaw members 16 and 18 (FIGS. 1 and 2A). For illustrative purposes, end effector 14 includes jaw members 16 and 18 that are configured to treat tissue via ultrasonic energy. Jaw member 16 is pivotable about the jaw member 18 (and/or the distal end 12 of the shaft 8) and movable relative thereto when lever or movable handle 20 is moved proximally. More particularly, jaw member 16 is movable from an open position for positioning tissue between the jaw members 16 and 18, to a clamping position for grasping tissue between the jaw members 16 and 18 and against jaw member 18. In the illustrated embodiment, jaw member 18 serves as an active or oscillating blade and is configured to treat tissue. To this end, jaw member 18 includes an ultrasonic member (not shown) that is operably coupled to a transducer 32 (FIGS. 1, 2A and 4), and an operating surface 22 (FIGS. 1 and 2A) configured to treat tissue. In the illustrated embodiment, the operating surface 22 is configured to transect, dissect and/or coagulate tissue upon actuation of an activation button 24 (FIGS. 1, 2A and 3).

Activation button 24 places the instrument 2 in two modes of operation, a low-power mode of operation and a high-power mode of operation. More particularly, activation button 24 is depressable to a first position for delivering low-power to the active jaw member 18 and a second position for delivering high-power to the active jaw member 18. In the first position, one or more audio or visual indicators may indicate to user that the activation button 24 is in the low-power mode. For example, and in one particular embodiment, an audio indicator may include a low-pitch, slow pulsating tone that indicates to a user that the activation button 24 is in the first position. Likewise, one or more audio or visual indicators (nor shown) may indicate to user that the activation button is in the high-power mode, e.g., an audio indicator may include a high-pitch, fast pulsating tone that indicates to a user that the activation button 24 is in the second position.

Figure 2B:
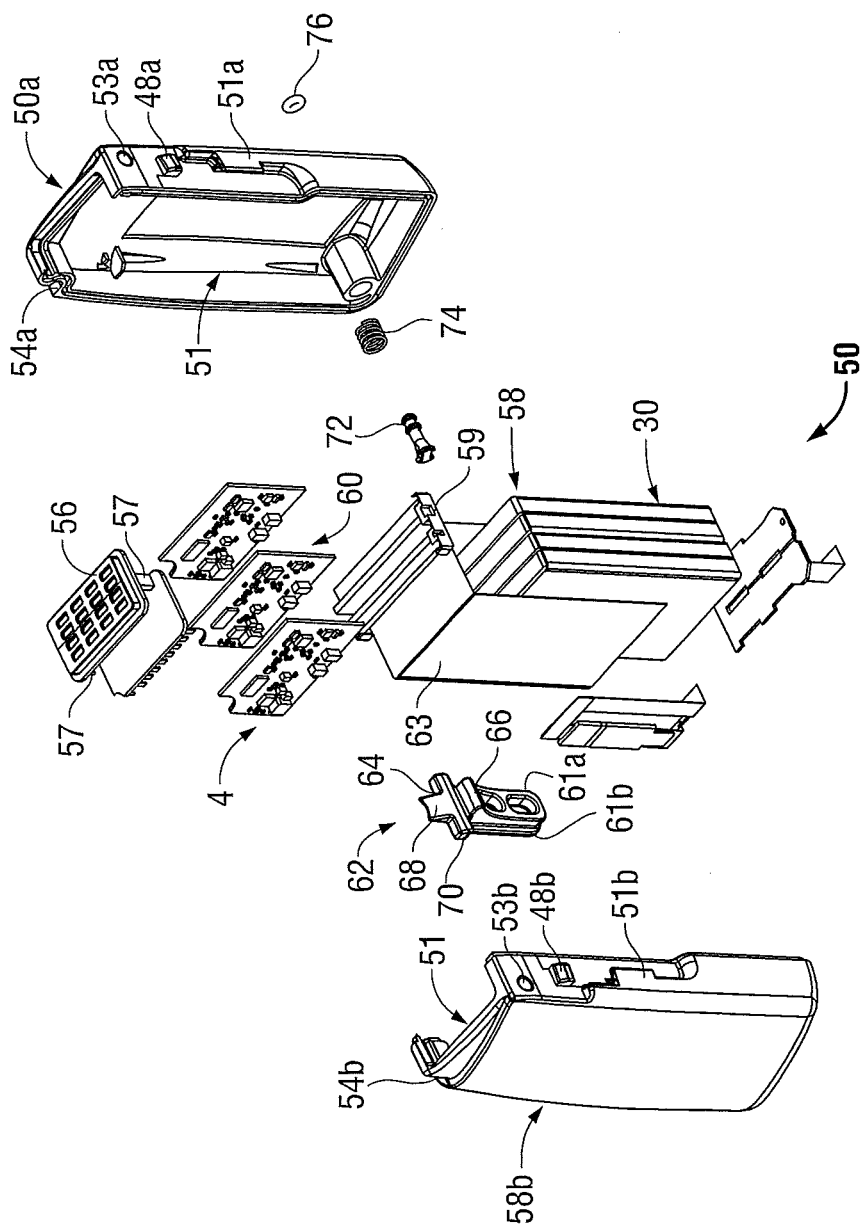
FIG. 2B is an enlarged perspective view of the area of detail indicated in FIG. 2A with parts separated.

Generator 28 (FIGS. 1, 2A, 3 and 4) is configured to convert electrical energy generated by a battery 30 (as best seen in FIG. 2B) of the battery assembly 4 to ultrasonic energy to drive the active jaw member 18.

Generator 28 operably couples to the housing 6 and may be selectively removable therefrom either in connection with removal of the battery 30 or independently. More specifically in the embodiment shown in FIGS. 1, 2A and 3, to secure the generator 28 to the housing 6, a user positions the generator 28 on a top portion of the housing 6 at a proximal end thereof and turns a torquing knob 36 (FIGS. 1, 2A, 3 and 4) in a clockwise direction and hand tightens the generator 28 to the housing 6. In certain embodiments, a torque wrench (not shown) may be utilized to facilitate turning the torquing knob 36.

Generator 28 includes transducer 32 (shown in phantom in FIGS. 1, 2A and 4) that is configured to convert electrical energy to mechanical energy that produces motion at an end of a waveguide 34 (shown in phantom in FIG. 1) that is in operative communication with the active jaw member 18. When the transducer 32 and waveguide 34 are driven at their resonant frequency, they produce mechanical motion at the active jaw member 18. The electronics of the generator 38 converts the electrical energy from the battery 30 into a high voltage AC waveform that drives the transducer 32. In one particular embodiment, the frequency of this AC waveform is the same as the resonant frequency of the waveguide 34 and transducer 32. As can be appreciated, the magnitude of the AC waveform includes a value that produces the proper amount of mechanical motion.

With reference again to FIG. 1, battery assembly 4 is configured to releasably couple to the housing 6. To this end, housing 6 includes a docking portion 40 (as best seen in FIGS. 2A and 3) defined therein. Docking portion 40 includes a generally elongated member 42 (see FIGS. 2A, 3 and 4) that extends in a generally perpendicular orientation with respect to a base member 44 and the longitudinal axis "A-A" (see FIGS. 2A, 3 and 4). The elongated member 42 includes one or more apertures 46 (see FIGS. 2A, 3 and 4) that are configured to releasably engage one or more corresponding protrusions 48a and 48b disposed on a handpiece 50 (FIG. 1 in combination with FIGS. 2A-3) of the battery assembly 4. Apertures 46 are disposed adjacent a bottom end of the elongated member 42 (FIG. 2). Positioning the apertures 46 as such facilitates latching and unlatching of the battery assembly 4 from the housing 6.

Figure 4:
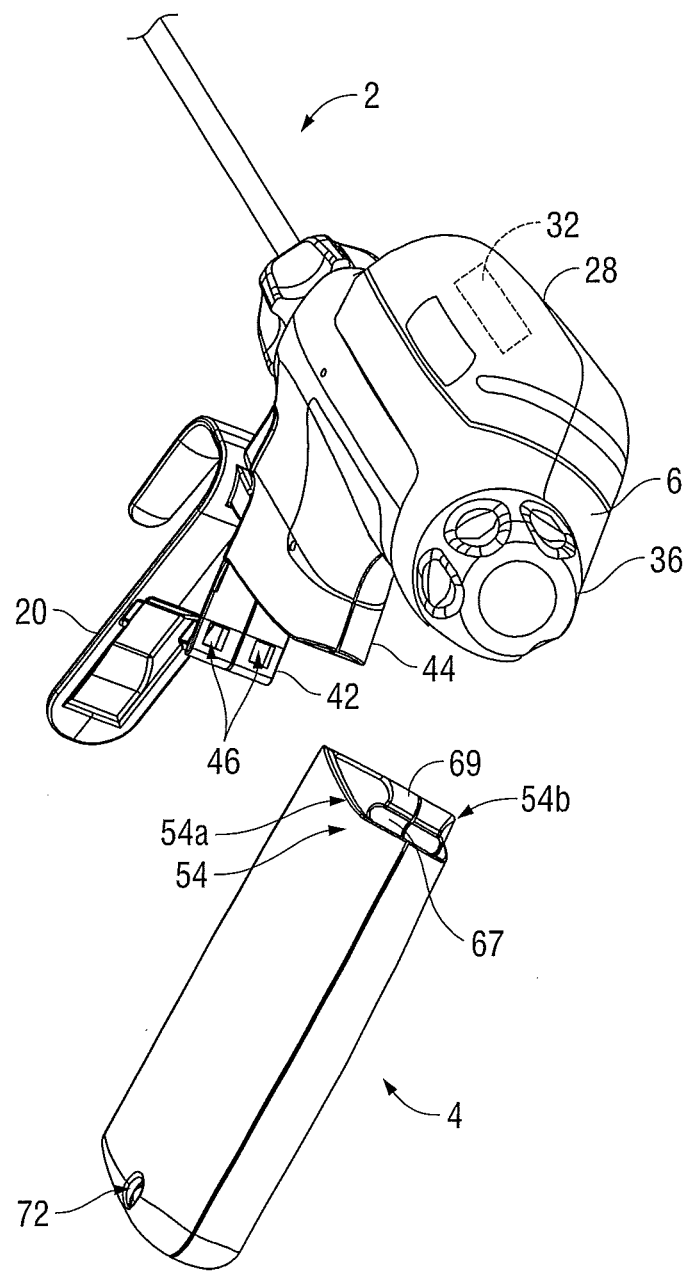
FIG. 4 is an end view of the battery powered surgical instrument depicted in FIG. 3.

Base member 44 is configured to releasably engage the battery assembly 4 and includes a protrusion 52 of suitable configuration (FIG. 3) operably disposed within and at a proximal end of the base member 44. The protrusion 52 is configured to releasably engage a corresponding pivot 54 that is disposed at a proximal end (or rear) of the handpiece 50 of the battery assembly 4 (as best seen in FIG. 4). Base member 44 includes electrical circuitry "EC" (see FIG. 3, for example) therein that is utilized to provide communication between the generator 28 and the battery 30.

Referring again to FIGS. 1-4, battery assembly 4 is illustrated. The overall mechanical architecture of the battery assembly 4 includes handpiece 50 having battery 30 operably disposed therein, see FIG. 2B.

Referring to FIG. 2B, handpiece 50, manufactured by any suitable manufacturing methods, may be made from any suitable material including, but not limited to plastic, plastic composites, metal, metal alloy, etc. In the illustrated embodiment, the handpiece 50 includes a contact cap 56 configured to facilitate electrical communication between the contact cap 56 and the electrical circuitry "EC" associated with the base member 44. The contact cap 56 may be made from Bayer Makrolon® 2885 polycarbonate with a 20% glass fiber filler.

With continued reference to FIG. 2B, handpiece 50 includes left and right clamshells 50a and 50b, respectively, that collectively define the handpiece 50 in the assembled configuration. The left and right clam shells 50a and 50b may be coupled together via one or more suitable coupling methods. In the illustrated embodiment, the left and right clam shells are ultrasonically welded together. Other forms and/or methods, e.g., soldering, of coupling the left and right clamshells 50 and 50b, respectively, to one another are contemplated. In the assembled configuration the left and right clamshells 50a and 50b, respectively, define an enclosure 51 that is configured to house battery assembly 30 including cells 58, printed circuit assemblies 60, and the contact cap 56. With this purpose in mind, each of the left and right clam shells 50a and 50b, respectively, includes a minimum wall thickness of 0.010 inches to about 0.080 inches. In the illustrated embodiment, the wall thickness of the respective left and right clamshells 50a and 50b is about 0.060 inches. The size of enclosure 51 is defined by the left and right clamshells 50a and 50b, respectively, provides internal "free space" adjacent to the cells 58. This "free space" is designed to accommodate the increase in thickness of the cells 58 as a result of charge and discharge cycles over the life of the battery assembly 4. That is, the cells 58 are allowed to "swell" uninterrupted into the "free space". In the assembled configuration, the handpiece 50 including the left and right clamshells 50a and 50b, respectively, are also configured to maintain the contact cap 56 in a substantially fixed orientation.

In the assembled configuration, the left and right clamshells 50a and 50b collectively define the pivot 54 at a proximal end (or rear) of the handpiece 50 (see FIG. 4). The pivot 54 is configured to releasably engage the protrusion 52 on the base member 44 such that the battery assembly 4 may be removably engaged with the instrument 2 and/or a charger (not shown) in a specific orientation. With this purpose in mind, the pivot 54 includes a notched area 67 that corresponds to the configuration of the protrusion 52 (FIG. 4). Pivot 54 also includes a lip 69 that is configured to removably and pivotably engage the protrusion 52 (FIGS. 3 and 4).

Each of the left and right clamshells 50a and 50b includes one or more dimples or indents 53a and 53b (FIGS. 2A and 2B) that are configured to releasably mate with corresponding detents that are operably disposed on a charger (not shown) that is configured to charge the battery 30 of the battery assembly 4.

Each of the left and right clamshells 50a and 50b includes respective protrusions 48a and 48b (FIGS. 2A and 2B) that are configured to releasably mate with the corresponding apertures 46 of the elongated member 42. The protrusions 48a and 48b are configured to remain engaged with the corresponding apertures 46 until a release latch 62 is moved into the extended position (FIG. 2A illustrates with aid of directional arrows the latch 62 in the extended position phantomly).

With reference again to FIGS. 1-2B, the release latch 62 is operably disposed at a distal end (or in the front of the handpiece 50). The release latch 62 may be made out of any suitable material hereinbefore described. In the illustrated embodiment, the release latch 62 is made out of polypropylene including a 15% glass fiber filler. The polypropylene with a 15% glass fiber filler material prevents and/or eliminates the effects of parasitic welding to the handpiece 50 during the ultrasonic weld assembly of the left and right clamshells 50a and 50b, respectively.

The release latch 62 provides a mechanism to remove the battery assembly 4 from the instrument 2. The release latch 62 is a "free-floating" part that is normally held in an "idle" or retracted position (FIGS. 1 and 2A) by the elongated member 42. In order to "de-mate" or uncouple the battery assembly 4 from the instrument 2, the release latch 62 is moved in a generally upward direction to the "use" or extended position (shown in phantom in FIG. 2A) that mechanically separates the battery assembly 4 and handpiece 50 from the instrument 2. In certain embodiments, a spring (not shown) may be utilized to bias the release latch 62 in the "idle" or retracted position.

Release latch 62 includes a generally elongated configuration having a top portion 64 (FIGS. 2A and 2B) configured to contact an interior or proximal wall of the elongated member 42 when the release latch 62 is moved to the extended position. To this end, the top portion 64 includes a slanted or angled ramp portion 68 that is configured to be wedged between the interior wall of the elongated member 42 and the distal end of handpiece 50 adjacent the two protrusions 48 located on the handpiece 50 (FIG. 2B). The top portion 64 also includes an elongated lateral bar portion 70 (FIG. 2B) that is configured to inhibit or prevent movement of the release latch 62 past a predetermined point. More particularly, the lateral bar portion 70 is configured to contact the protrusions 48a and 48b when the release latch 62 is moved a predetermined distance to the extended position.

Release latch 62 includes a bottom portion 66 (FIGS. 2A and 2B) that is ergonomically configured to receive a finger, e.g., a thumb, of a user. In the illustrated embodiment, bottom portion 66 includes a generally ramp-like configuration at distal end thereof. Left and right sides 61a and 61b of the bottom portion 66 are slidably coupled to corresponding left and right flanges 51a and 51b that are operably disposed on the respective left and right clamshells 50a and 50b of the handpiece 50. The left and right sides 61a and 61b and corresponding left and right flanges 51a and 51b collectively allow a user to move the release latch 62 from the retracted position to the extended position (and vice versa) while keeping the release latch 62 attached to the handpiece 50.

Continuing with reference with FIG. 2B, the contact cap 56 has metal electrical contacts insert molded to form a homogenized part. The contact cap 56 may be coupled or sealed to the handpiece 50 by any suitable coupling or sealing methods including, but not limited to soldering, welding, application of an adhesive, etc. In the illustrated embodiment, the contact cap 56 is sealed to the handpiece 50 with a light cure potting adhesive.

One or more ribs 57 and a frame 59 are operably disposed within the battery assembly 4 and are configured to collectively maintain the printed circuit assemblies 60 in a substantially fixed configuration when the left and right clam shells 50a and 50b are in the assembled configuration (FIG. 2B). More particularly, one or more ribs 57 are operably disposed on an underside of the cap 56 and frame 59 is operably disposed on a top portion of a sleeve 63 that is configured to house one or more cells (3 lithium polymer cells) of the battery 30.

An over pressure safety vent 72 (FIG. 2B) may be located on one or both of the left and right clamshells 50a and 50b. For illustrative purposes, the over pressure safety vent or valve 72 is located on the left clam shell 50a. To maintain the fluid-tight seal, the over pressure safety valve 72 is secured to the left clamshell 50a via a spring 74 and an o-ring 76 (FIG. 2B). The spring 74 biases the over pressure safety valve 72 against the o-ring 76. Pressure is released through over pressure safety valve 72 once a predetermined pressure is reached and/or exceeded inside the handpiece 50.

In use, the battery assembly 4 is, initially, coupled to a charger (not shown). To attach the battery assembly 4 to the instrument 2, a user positions the pivot 54 adjacent the protrusion 52 and "swings" the distal end of the handpiece 50 toward the elongated member 42 of the docking portion 40. The protrusions 48a and 48b engage the apertures 46. In the engaged condition, the release latch 62 is in the retracted position (FIGS. 1 and 2A). To disengage the battery assembly 4 from the instrument 2, a user moves the release latch 62 upward to the extended position (shown in phantom in FIG. 2A). Upward movement of the release latch 62 causes the ramp portion 68 of the top portion 64 to be wedge between the interior wall of the elongated member 42, which, in turn, causes the protrusions 48a and 48b to disengage from the apertures 46.

The unique configuration of the battery assembly 4 including the pivot 52, release latch 62 and protrusions 48a and 48b that releasably couple to the apertures 46 on the elongated member 42 of the docking portion 42 allows a user to conveniently and easily attach and detach the battery assembly 4 from the instrument 2.

The instrument 2 and battery assembly 4 may be configured to releasably couple to one another via one or more alternate coupling methods.

For example and with reference to FIGS. 5A and 5B, an alternate embodiment of a portable surgical the instrument is designated instrument 102. Instrument 102 is configured to releasably couple to a battery assembly 104. Instrument 102 and battery assembly 104 are substantially identical to instrument 2 and battery assembly 4. In view thereof, and so as not to obscure the present disclosure with redundant information, only those features that are unique to instrument 102 and battery assembly 104 are described herein.

Unlike instrument 2, instrument 102 does not include a docking portion 40 having an elongated member 42. More particularly, instrument 102 includes a housing 106 having a base member 144 (shown partially separated from the housing 106) that includes one or more flexible arms or "claws" 103. For illustrative purposes, base member 144 is shown including 4 "claws" 103a-103d.

Claws 103a-103d may be made from any suitable materials including, but not limited to metal, metal alloy, plastic, plastic composites, one of the aforementioned materials, etc. In the embodiment illustrated in FIGS. 5A and 5B, claws 103a-103d are made from metal.

Claws 103a-103d are configured to releasably engage the battery assembly 104. To this end, claws 103a-103d are pivotably coupled to the base member 144 via one or more coupling methods, e.g., pivot pins or hinges not explicitly shown. The claws 103a-103d include respective bottom portions configured to engage a bottom portion of the battery assembly 104. More particularly, the claws 103a-103d include respective bottom portions 105a-105d each having a generally square shape. When the claws 103a-103d are in the closed or engaged position, the claws 103a-103d collectively form a generally square-like shape, as best seen in FIG. 5B. In the engaged position the claws 103a-103d are configured to "lock" the battery assembly 104 in the engaged position.

In certain embodiments, the claws 103a-103d may be configured to translate within the base member 144; this may facilitate maintaining the battery assembly 104 in the locked or engaged position and/or engaging the contact cap 56 of the battery assembly 104 with the electrical circuitry of the base member 144.

Unlike battery assembly 4, battery assembly 104 does not include a release latch 62. More particularly, the battery assembly 104 is positionable between the claws 103a-103d and is configured to engage the base member 144 when the claws 103a-103d are moved to the closed or engaged position. In the closed or engaged position the battery assembly 104 communicates with the electrical circuitry disposed within the base member 144.

In the embodiment illustrated in FIGS. 5A and 5B, to facilitate engaging and disengaging the claws 103a-103d from the battery assembly 104, claws 103a-103d are configured to mate with corresponding grooves or notches 106a-106d that are operably disposed on an exterior surface the battery assembly 104 (FIG. 5A).

In use, the claws 103a-103d are, initially, in the open position (FIG. 5A). To couple the battery assembly 104 to the instrument 102, a user positions the battery 104 between the claws 103a-103d. In certain embodiments, the claws 103a-103d engage the corresponding grooves 105a-105d. A user then moves the claws 103a-103d to the closed position (FIG. 5B). In certain embodiments, a user may, subsequently, move the claws 103a-103d upward and into the base member 144 to lock the battery assembly 104 into the claws 103a-103d.

Figure 6A:
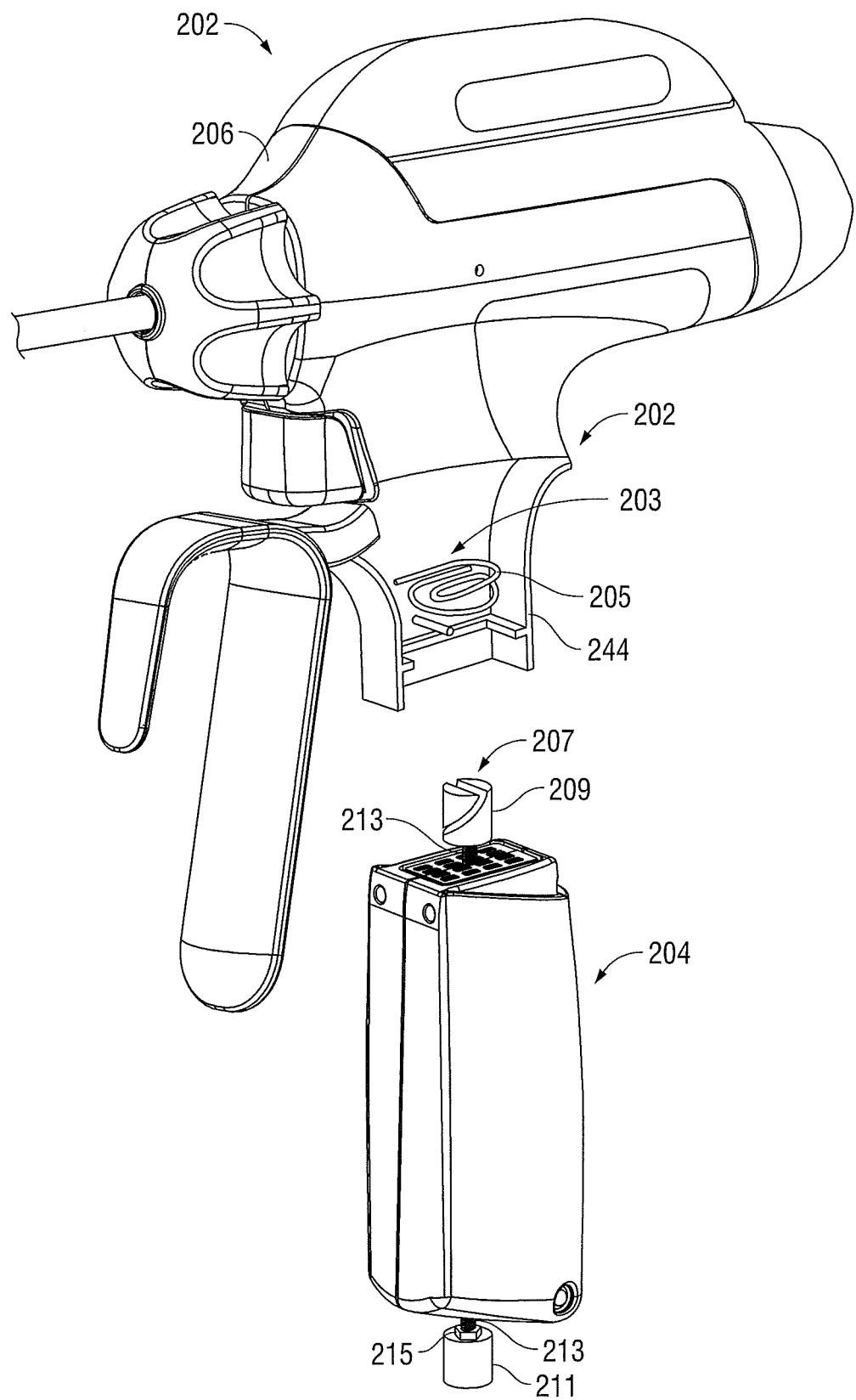

With reference to FIGS. 6A-6C, another embodiment of a portable surgical instrument is designated instrument 202. Instrument 202 is configured to releasably couple to a battery assembly 204. Instrument 202 and battery assembly 204 are substantially identical to instrument 2 and battery assembly 4. In view thereof, and so as not to obscure the present disclosure with redundant information, only those features that are unique to instrument 202 and battery assembly 204 are described herein.

A lock 203 in the form of a guide rail 205 is operably disposed within base member 244 of a housing 206 of the instrument 202 (FIGS. 6A-6C). More particularly, the guide rail 205 is configured to releasably engage a corresponding groove 207 (FIGS. 6A-6C) defined along a periphery of a lock bolt 209 (FIGS. 6A-6C) that is coupled to the battery assembly 204. The guide rail 205 may be formed from any materials described hereinbefore, e.g., plastic. The guide rail 205 may include any suitable configuration. In the illustrated embodiment, the guide rail includes a generally helical configuration having a diameter that is configured to receive the lock bolt 209 therethrough (see FIGS. 6B-6C).

A knob 211 (FIGS. 6A-6C) is operably coupled to the battery 204 and is rotatable with respect thereto in a clockwise and counterclockwise direction. In the illustrated embodiment the knob 211 is configured to turn the lock bolt 209 such that the lock bolt 209 either engages or disengages the guide rail 205. In the illustrated embodiment, the knob 211 is turned a ¼ of a full turn in either the clockwise or counterclockwise direction to engage or disengage the lock bolt 209 to and from the guide rail 205, respectively.

A threaded rod 213 (FIGS. 6A-6C) extends through the length of the battery assembly 204 and is configured to operably couple the lock bolt 209 to the knob 211. More particularly, the threaded rod 213 extends the length of the battery assembly 204 and couples thereto via a lock nut 215 that is disposed adjacent the knob 211 (FIGS. 6A-6C). The lock nut 215 is configured to facilitate turning the lock bolt 209 while maintaining engagement of the threaded rod 213 to the battery assembly 204.

In use, the battery assembly 204 is, initially, coupled to a charger (not shown). To attach the battery assembly 204 to the instrument 202, a user positions the lock bolt 209 within the guide rail 205 and turns the knob 211a a ¼ turn in the clockwise direction, which, in turn, rotates the lock bolt 209 such that the lock bolt 209 engages the guide rail 205 (FIG. 6C). To disengage the battery assembly 204 from the instrument 202, a user turns the knob 211 a ¼ turn in the counter clockwise direction, which, in turn, rotates the lock bolt 209 such that the lock bolt 209 disengages the guide rail 205 (FIG. 6B).

With reference to FIGS. 7A-7B, another embodiment of a portable surgical instrument is designated instrument 302 which is configured to releasably couple to a battery assembly 304. Instrument 302 and battery assembly 304 are substantially identical to instrument 2 and battery assembly 4. In view thereof, and so as not to obscure the present disclosure with redundant information, only those features that are unique to instrument 302 and battery assembly 304 are described herein.

In the embodiment illustrated in FIGS. 7A-7B, the battery assembly 304 magnetically couples to a base member 344 of a housing 306 via a magnetic mechanism 305 that is operably associated with each of the battery assembly 304 and the base member 344. More particularly, the magnetic mechanism 305 includes one or more magnets 307 (or magnetic materials) on the battery assembly 304 and one or more magnets 309 (or magnetic materials) on or within the base member 344. For illustrative purposes, the magnets 309 are shown within the base member 344. The magnets 307 and 309 on the respective battery assembly 304 and the base member 344 have opposite polarities. In the embodiment illustrated in FIGS. 7A and 7B, one or both of the magnets 307 and 309 is/are an electromagnet that is capable of changing polarities. For illustrative purposes, the magnet 309 within the base member 344 is illustrated as the electromagnet.

An actuator 311 (FIGS. 7A and 7B) is operably disposed on the instrument 302 and is in operative communication with the magnet 309. The actuator 311 is configured to change a polarity of magnet 309 for locking and unlocking the battery assembly 304 to and from the instrument 302.

In the embodiment illustrated in FIGS. 7A and 7B, to facilitate coupling the battery assembly 304 to the base member 344, the battery assembly 304 includes a flanged bottom portion 321. The flanged bottom portion 321 provides a gripping surface for a user.

In use, the battery assembly 304 is, initially, coupled to a charger (not shown). To attach the battery assembly 304 to the instrument 302, a user positions the battery assembly 304 into the base member 344. The opposite polarities of the magnets 307 and 309 maintain the battery assembly 304 and instrument 302 in the engaged or locked position (FIG. 7B). To disengage the battery assembly 304 from the instrument 302, a user presses the actuator 311 to change the polarity of the magnet 309 to an opposite polarity of the magnet 307, which, in turn, allows the user to remove the battery assembly 304 from the base member 344.

Alternatively, the magnetic mechanism 305 may be configured such that a user may simply "pry" the magnets 307 and 309 apart as needed. That is, the magnets 307 and 309 may be configured to maintain the battery assembly 304 and the instrument 302 in an engaged or locked position until a predetermined amount of force, i.e., a force greater than the magnet force coupling the battery assembly 304 to the instrument 302, is applied to the battery assembly 304 and/or instrument 302.

With reference to FIGS. 8A-8B, another embodiment of a portable surgical instrument is designated instrument 402. Instrument 402 and battery assembly 404 are substantially identical to instrument 2 and battery assembly 4. In view thereof, and so as not to obscure the present disclosure with redundant information, only those features that are unique to instrument 402 and battery assembly 404 are described herein.

An adhesive is operably coupled to either a battery assembly 404 or a base member 444 of a housing 406. The adhesive is configured to couple the battery assembly 404 including the battery 30 to a housing 406. In the embodiment illustrated in FIGS. 8A-8B, the adhesive is a low tack adhesive, such as, for example, a low tack adhesive tape 421. The low tack adhesive tape 421 is operably disposed adjacent a contact cap 460 of the battery assembly 404 and includes a grid-like configuration similar to that of the contact cap 460. More particularly, the low tack adhesive tape 421 is fixedly coupled to the battery assembly 404 and substantially surrounds the grid of the contact cap 460. The low tack adhesive tape 421 is configured to stick to an internal surface of the base member 444. In the embodiment illustrated in FIGS. 8A and 8B, the low tack adhesive tape 421 is configured to stick to an internal area of the base member 444 adjacent the electrical circuitry "EC" contained therein. As can be appreciated, the low tack adhesive tape 421 is configured to stick to the internal area of the base member in a manner that does not interfere with the operation of the electrically circuitry "EC."

A removable film (not shown) covers or protects the low tack adhesive tape 421 when the battery assembly 404 is not coupled to the instrument 402. Accordingly, the "tackiness" of the low tack adhesive tape 421 is not compromised when the battery assembly 404 is not coupled to the instrument 402 and ensures that the low tack adhesive tape 421 provides the required amount of "tackiness" and/or "sticking" power.

To attach the battery assembly 404 to the instrument 402, a user removes the film from the low tack adhesive tape 421 and positions the battery assembly 404 within the base member 444 of the instrument 402. To remove the battery assembly 404 from the instrument 402, a user simply "pries" or pulls the battery assembly 404 from the base member 444.

Figure 9:
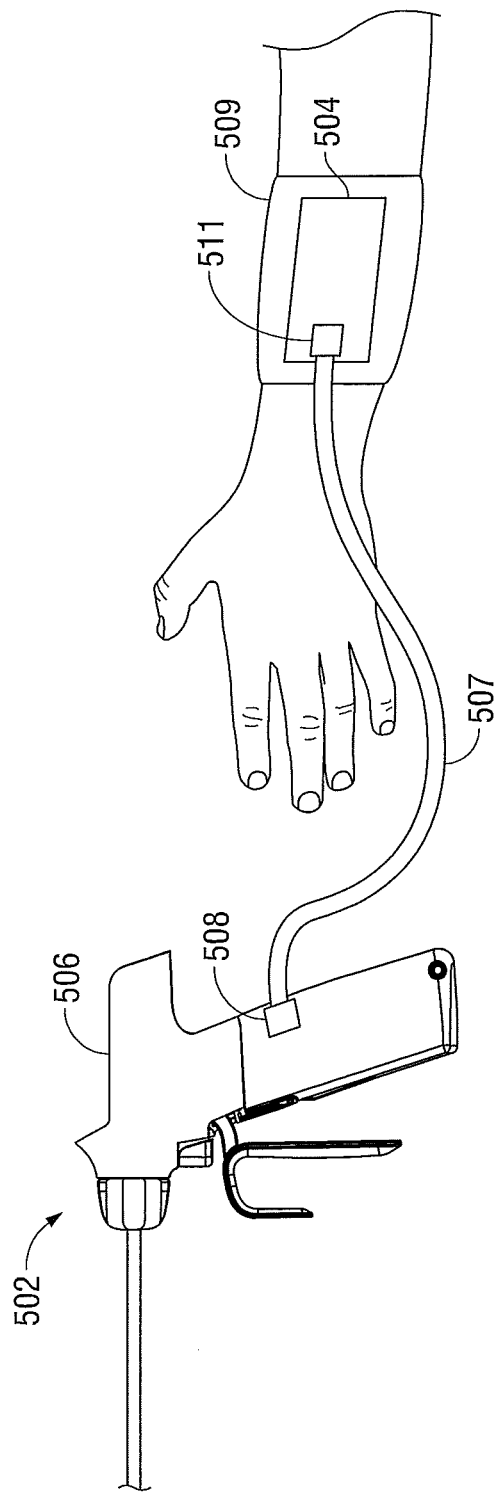
FIG. 9 is a schematic view of a battery powered surgical instrument configured for use with a removable battery assembly according to still another embodiment of the present disclosure.

With reference to FIG. 9, another embodiment of a portable surgical instrument is designated instrument 502. Instrument 502 and battery assembly 504 are substantially identical to instrument 2 and battery assembly 4. In view thereof, and so as not to obscure the present disclosure with redundant information, only those features that are unique to instrument 502 and battery assembly 504 are described herein.

The battery assembly 504 remotely attaches to a housing 506 of the instrument 502 via one or more suitable coupling methods including, but not limited to a wire, cable, cord, USB, etc. For illustrative purposes, a cable 507 provides electrical communication between the instrument 502 and battery assembly 504. The housing 506 includes a port 508 thereon that is configured to connect to an end of the cable 507. Likewise, a port 511 is disposed on the battery assembly 504 and is configured to receive an end of the cable 507.

In the embodiment illustrated in FIG. 9, the battery assembly 504 is configured to removably attach to an arm of a user. More particularly, a holding device or harness 509 is configured to removably attach to an arm of a user and configured to house the battery assembly 504 therein. One or more straps (not shown) may be coupled to the harness 509 and utilized to attach the harness 509 to the arm of a user. For example, and in some embodiments, two straps fitted with Velcro® may be utilized to secure the harness 509 to an arm of a user.

To couple the battery assembly 504 to the instrument 502, the cable 507 is coupled to each of the ports 511 and 508 on the battery assembly 504 and the housing 506, respectively. Subsequently, the battery assembly 504 is positioned on or attached to the harness 509 that is attached to a user. To uncouple the battery assembly 504 from the instrument 2, a user simply removes the cable from the port 511 and/or the port 508 of the respective battery assembly 504 and instrument 502.

Alternatively, the battery assembly 504 may be simply positioned adjacent or in the vicinity, e.g., on the operating table, of the instrument 502. The exact positioning of the battery assembly 504 with respect to the instrument 502 may depend on the length of the cable 507 provided, the surgical procedure, etc.

With reference to FIGS. 10A and 10B, another embodiment of a portable surgical instrument is designated instrument 602. Instrument 602 and battery assembly 604 are substantially identical to instrument 2 and battery assembly 4 and only those features that are unique to instrument 602 and battery assembly 604 are described herein.

In the embodiment illustrated in FIGS. 10A and 10B, a housing 606 includes a docking member 640 that is made from an elastomeric material, such as, for example, polychloroprene. The docking member 640 includes an elongated configuration with a generally oval shape having an open sidewall 642 defined therein that is configured to receive and releasably house the battery assembly 604 therein.

To facilitate connecting a contact cap, e.g., contact cap 56, of the battery assembly 604 with the electrical circuitry "EC" contained within a base member 644, the battery assembly 604 may include a length that is slightly larger than a length of the docking member 640. Thus, when the battery assembly 604 is positioned within the docking member 640, the docking member 640 exerts an upward force on the battery assembly 604 such that the contact cap 56 contacts and remains in electrical communication with the electrical circuitry "EC" contained within the base member 644.

In use, to couple the battery assembly 604 to the instrument 602, the battery assembly 604 is positioned within the docking member 640. To remove the battery assembly 604 from the docking member 640, a user grasps the battery assembly 604 and "pries" or pulls the battery assembly 604 therefrom.

Figure 11A:
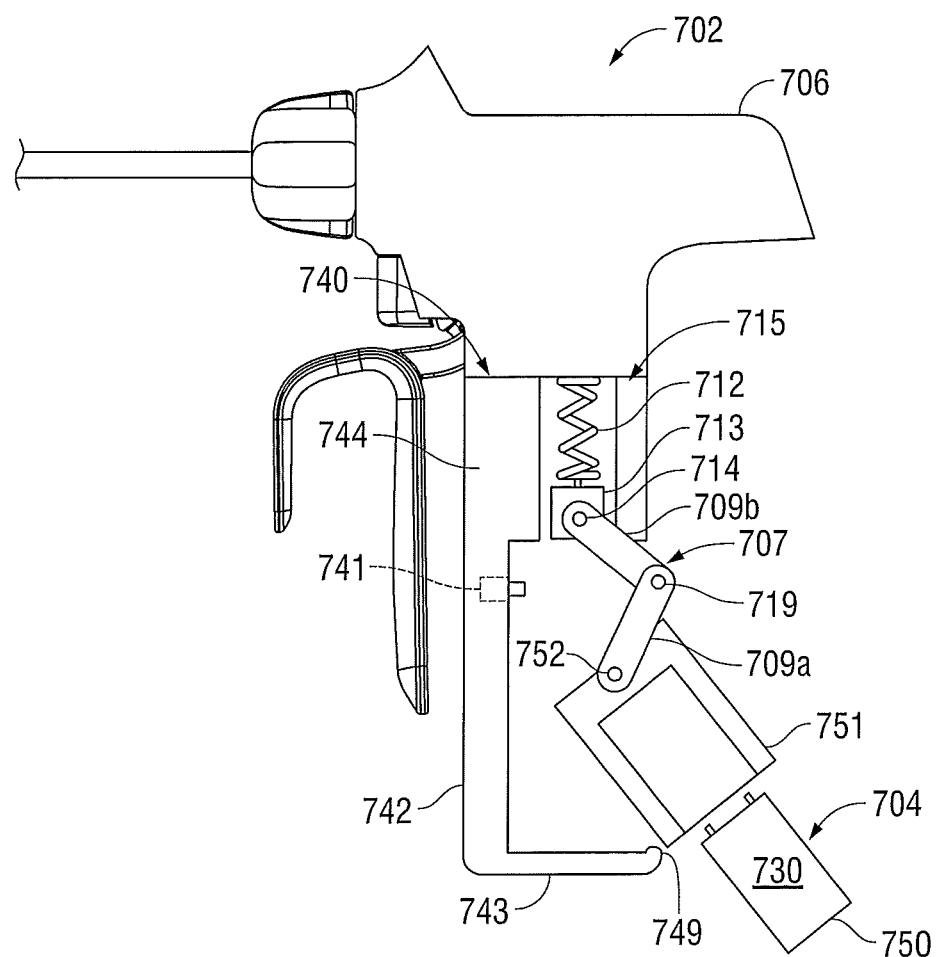
FIGS. 11A-11C are schematic views of a battery powered surgical instrument configured for use with a removable battery assembly according to still another embodiment of the present disclosure.
Figure 11C:
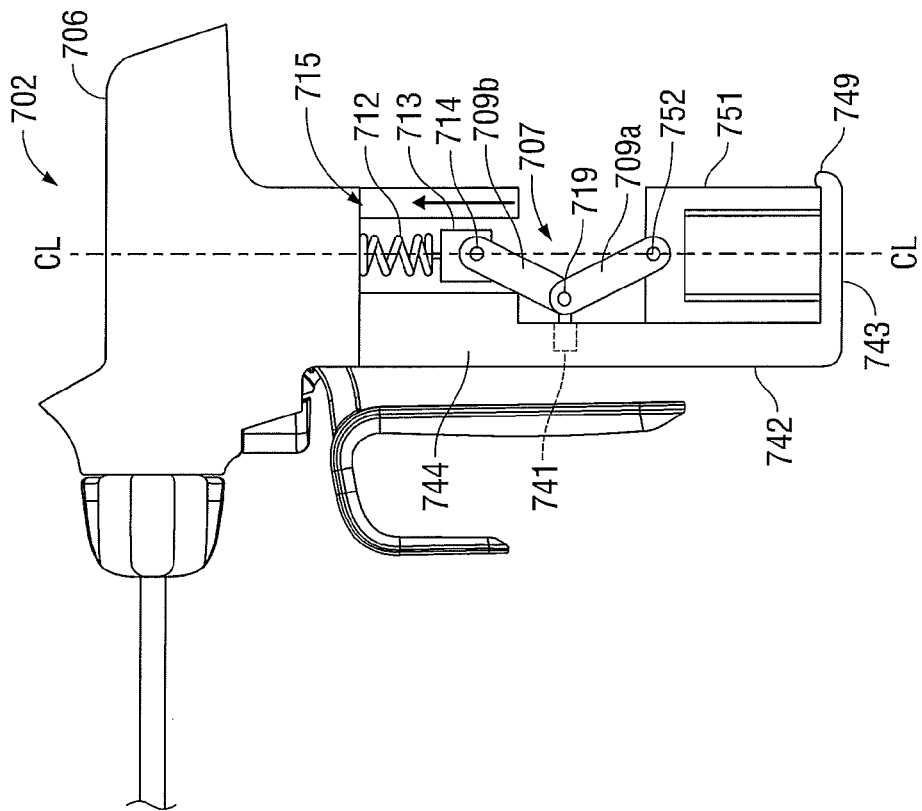
Figure 11B:
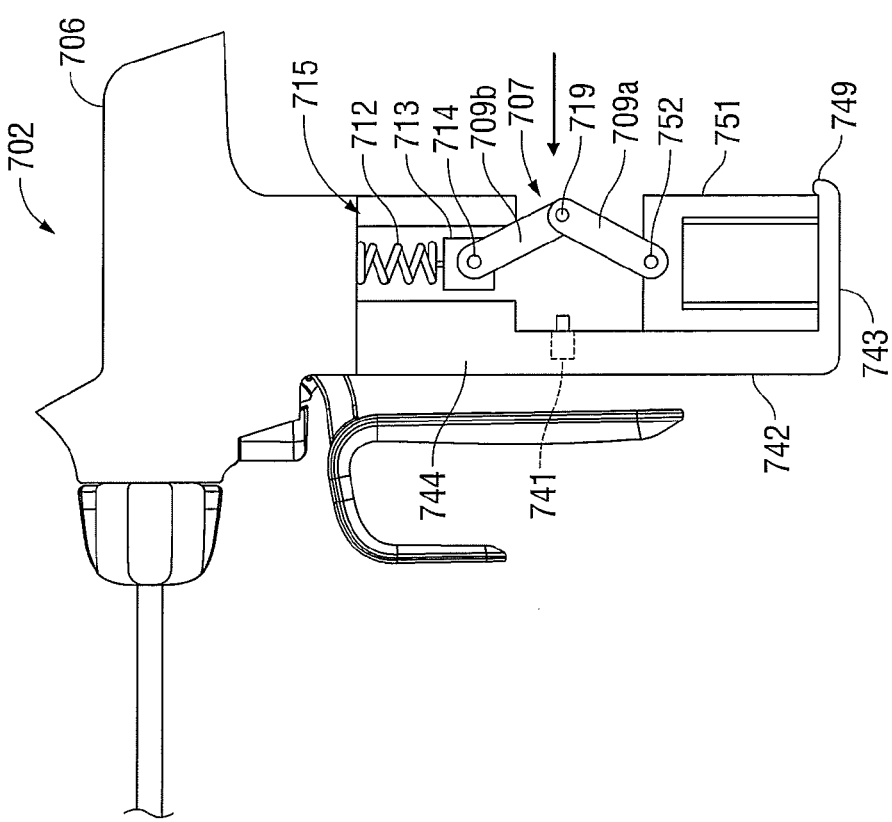

With reference to FIGS. 11A-11C, another embodiment of a portable surgical instrument is designated instrument 702. Instrument 702 and battery assembly 704 are substantially identical to instrument 2 and battery assembly 4 and only those features that are unique to instrument 702 and battery assembly 704 are described herein.

A docking portion 740 (FIG. 11A) includes an elongated member 742 that is disposed generally perpendicularly with respect to the longitudinal axis "A-A" and a bottom portion 743 that is configured to engage a corresponding bottom portion of a handpiece 750 of the battery assembly 704.

A release mechanism 741 is operably disposed on the elongated member 742 of the docking portion 740 and is configured to disengage the handpiece 750 including a battery 730 of the battery assembly 704 from the docking portion 740. More particularly, the release mechanism 741 is translatable along the longitudinal axis "A-A" and is configured to "push" the battery assembly 704 proximally and out of a locked position and/or engagement with the docking portion 740 when release mechanism 741 is actuated. A spring (not shown) may be operably coupled to the release mechanism 741 and may be configured to bias the release mechanism 741 in an initial position, e.g., a non-actuated position.

A linkage system in the form of an over-center linkage mechanism 707 is operably disposed in base member 744 of the docking portion 740. The linkage system 707 includes one or more over-center links that pivot about another. In the embodiment illustrated in FIGS. 11A-11C, two (2) over-center links 709a and 709b are shown pivotable about one another. Link 709b is operably coupled to a biasing member 712 for biasing the links 709a, 709b in locked configuration in the docking portion 740, see FIG. 11C, for example.

Links 709a, 709b are configured to selectively engage either the handpiece 750 or the battery 730. In particular, the link 709a couples via a pivot pin 752 to a housing 751 that is shaped to complement the handpiece 750 (or the battery 730) of the battery assembly 704 (FIGS. 11A-11C). The pivot pin 752 allows the battery assembly 704 to pivot about the link 709a when the battery assembly 704 is being "loaded" into the docking portion 740 (FIGS. 11A-11B). In some embodiments, it may prove useful for the battery assembly 704 and link 709a to be fixedly coupled to one another, i.e., not pivotably coupled to one another.

Housing 751 is configured to communicate with the electrical circuitry in the housing 706 such that when the battery assembly 704 is coupled to the housing 751, the battery 704 is capable of providing electrical energy to the generator 28.

The link 709a pivotably couples to link 709b via one or more suitable coupling methods. In the embodiment illustrated in FIGS. 11A-11C, a pivot pin 719 is operably disposed at a bottom end of the link 709b and operably couples to an aperture 720 (shown engaged with the pivot pin 719 and as such not explicitly shown) disposed at a top end of the link 709a.

Link 709b includes a generally elongated configuration having a piston head 713 of suitable configuration operably coupled at a top end thereof (FIGS. 11A-11C) via a pivot pin 714. The piston head 713 includes a generally cylindrical configuration having a top surface thereof operably coupled to the biasing member 712 by one or more suitable coupling methods, e.g., soldering.

The biasing member 712 may be any suitable biasing member including a spring, resilient member, etc. The biasing member 712 is in the form of a compression spring that is operably disposed within an elongated or longitudinal cavity or slot 715 of the base member 744. The biasing member 712 including the piston head 713 of the link 709b is configured to translate within the longitudinal slot 715. More particularly, the biasing member 712 including the piston head 713 is configured to translate from an normally extended position that corresponds to the link 709a being in the unlocked position (FIG. 11A), to a retracted position that corresponds to the link 709a being coupled to the battery assembly 704 and in the locked position (FIG. 11C). That is, in the locked position, the link 709a will be disposed past a center-line "CL" (FIG. 11C). The link 709a is configured to remain in the locked position under the biasing force provided by the spring 712 until a user actuates the release mechanism 741.

In use, to couple the battery assembly 704 to the instrument 702, a user loads the battery assembly 704 into the housing 751. Then, a user pivots the housing 751 and positions the housing 751 including the battery assembly 704 therein into the docking portion 740 (FIG. 11B). To lock the housing 751 into the docking portion 740, a user pushes the links 709a, 709b distally toward the docking portion 740 (FIG. 11B). As the biasing member 712 including the piston head 713 translates to the retracted position, the links 709a, 709b transition past vertical, e.g., "over-center," and past the "CL" to the locked position that corresponds to the battery assembly 704 being latched or coupled to the docking portion 740 of the instrument 702 (FIG. 11C).

To unlatch the battery assembly 704 from the instrument 2, a user may move the release mechanism 741 proximally to push the battery assembly 704 out of the locked position and/or engagement with the docking portion 740.

Figure 12A:
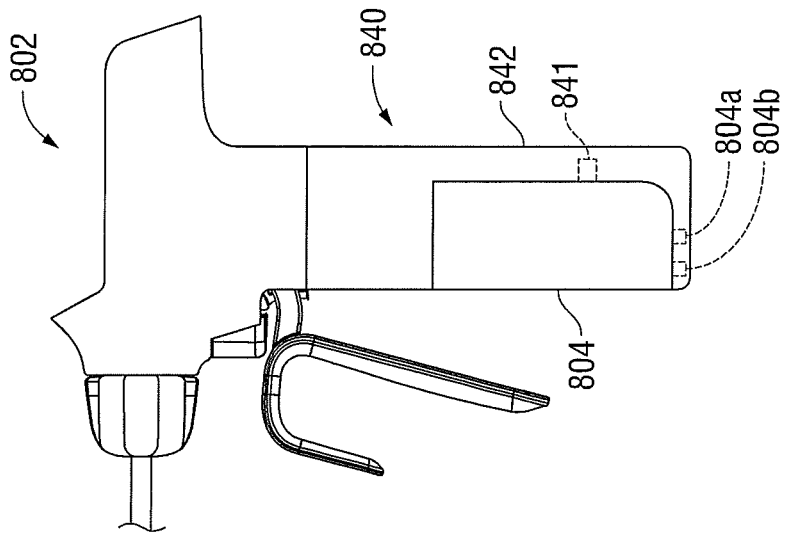
FIGS. 12A-12D are schematic views of a battery powered surgical instrument configured for use with a removable battery assembly according to still another embodiment of the present disclosure.
Figure 12B:
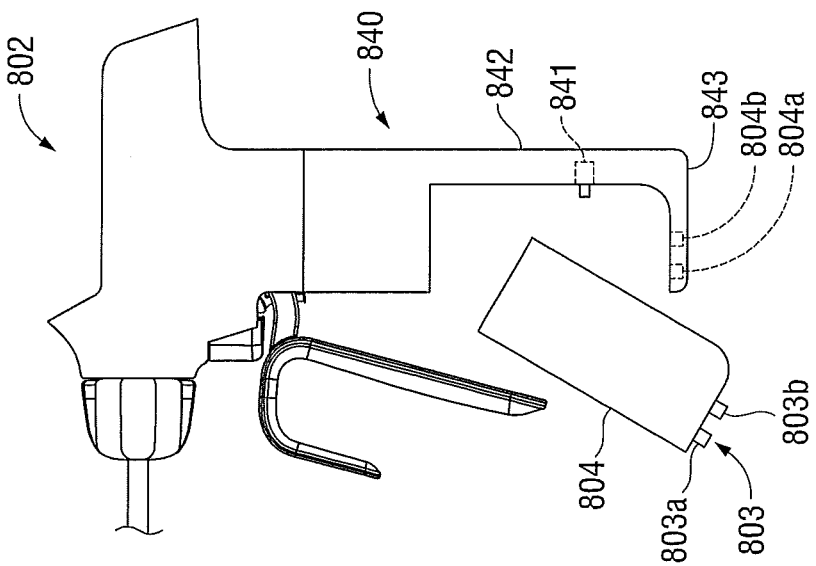
Figure 12D:
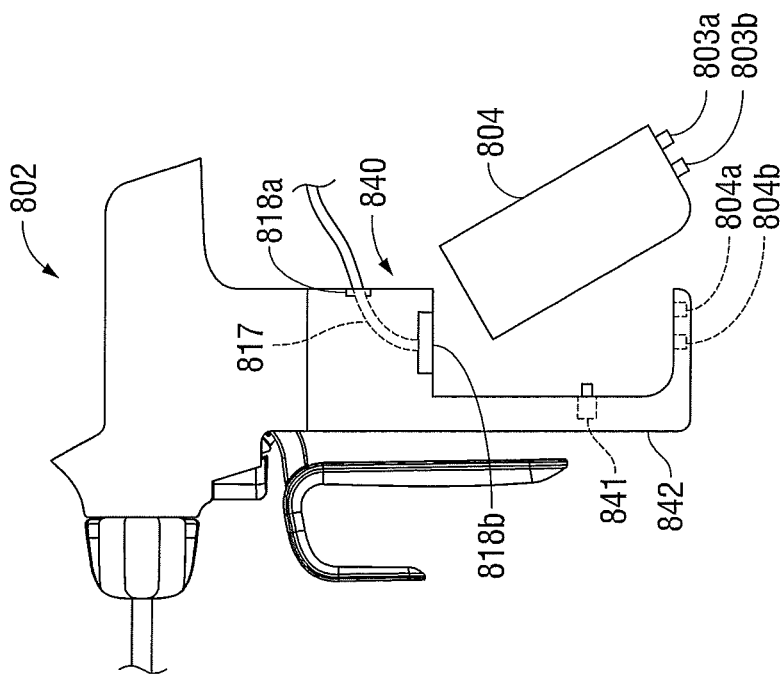
Figure 12C:
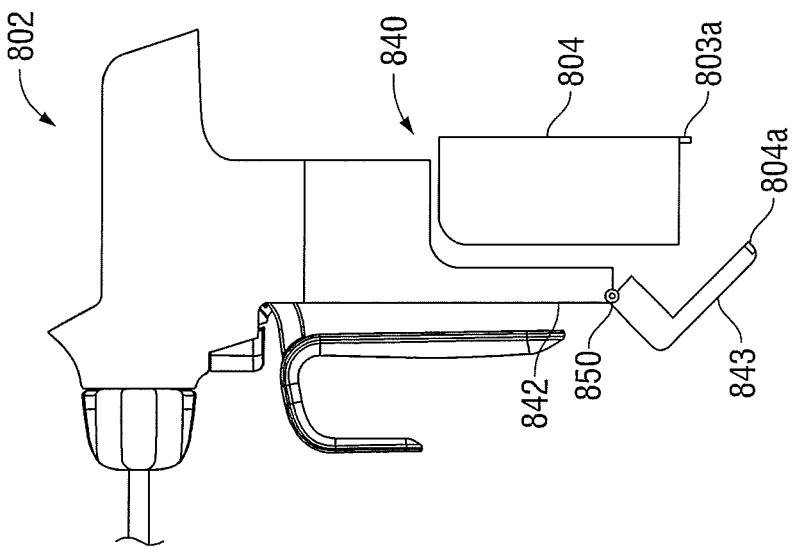

With reference to FIGS. 12A-12C, other embodiments of a portable surgical instrument are designated instrument 802. Instrument 802 is configured to releasably couple to a battery assembly 804. Instrument 802 and battery assembly 804 are substantially identical to instrument 2 and battery assembly 4 and only those features that are unique to instrument 802 and battery assembly 804 are described herein.

A bottom portion of the battery assembly 804 includes one or more latching members 803. In the embodiment illustrated in FIGS. 12A and 12B, the latching members 803 include two protrusions or detents 803a and 803b that are configured to releasably engage two corresponding apertures or indents 804a and 804b that are operably disposed on a bottom portion 843 of a docking portion 840.

A release mechanism 841 (shown in phantom in the representative figures) is disposed on an elongated member 842 of the docking portion 840 and is configured to disengage the detents 803a and 803b from the indents 804a and 804b of the docking portion 840. The release mechanism 841 may be any suitable release mechanism such as, for example, a slide lever, push-button or the like. In the embodiment illustrated in FIGS. 12A, 12B and 12D, the release mechanism 841 is in the form of a slide lever. Release mechanism 841 is translatable along the longitudinal axis "A-A" and is configured to "push" the battery assembly 804 out of a locked position and/or engagement with the docking portion 840 when release mechanism 841 is actuated. A spring (not shown) may be operably coupled to the release mechanism 841 and configured to bias the release mechanism 841 in an initial position, e.g., a non-actuated position.

The docking portion 840 may be configured for rear loading (FIGS. 12A and 12B) or, in certain embodiments, front loading, see FIG. 12D for example.

In use, to couple the battery assembly 804 to the instrument 802, a user positions the battery assembly 804 into the docking portion 840 of the instrument 2 such that the detents 803a and 803b engage the corresponding indents 804a and 804b. Engagement of the detents 803a and 803b with the corresponding indents 804a and 804b secures and/or locks the battery assembly 804 to the instrument 802 (FIG. 12B). To unlock or unlatch the battery assembly 804 from the instrument 802, a user moves the release mechanism 841 either distally (FIG. 12A) or proximally (FIG. 12D); this of course will depend on if the instrument 802 is configured for rear or front loading, respectively.

In some embodiments, the bottom portion 843 of the docking portion 840 may be pivotably coupled to the elongated member 842 (see FIG. 12C for example). For example, a hinge 850 of suitable configuration may operably couple the elongated member 842 to the bottom portion 843. In this instance, the hinge 850 is movable from an unlatched position (FIG. 12C) for loading the battery assembly 804 to the docking portion 840, to a latched position (not shown) for locking the battery assembly to docking portion 840. In the embodiment illustrated in FIG. 12C, one or more detents, e.g., detent 803a, may be configured to releasably couple to one or more corresponding indents, e.g., indent 804a. Each of the detents and indents 803a and 804a, function as previously described.

In the instance were the bottom portion 843 and elongated member 842 are pivotably coupled to one another, a user unlatches the bottom portion 843 to position the battery assembly 804 into the docking portion 842. Subsequently, the bottom portion 843 is moved back to the locked or latched position to secure the battery assembly 804 to the instrument 2.

To facilitate securing or locking the battery assembly 804 (or any of the previously described battery assemblies) to the instrument 802 (or any of the previously described instruments), the instrument 802 may be configured to operably couple to a remote suction device, such as, for example, a hospital suction source, see FIG. 12D for example. In this instance, a lumen 817 (illustrated in phantom in FIG. 12D) extends through the housing 806 and may be in fluid communication with the hospital suction source via a proximal end that is configured to couple to the remote suction source, e.g., via a proximal port 818a, and a distal end that is configured to draw the battery assembly 804 into the docking portion 840, e.g., via a distal port 818b.

In use, when the battery assembly 804 is positioned in the docking portion 840, the remote suction source, e.g., the suction provided by the hospital suction source, helps draw the battery assembly 804 into the docking portion 804 and helps maintain a secured and/or fixed relationship between the battery assembly 804 and in the instrument 802.

Figure 13A:
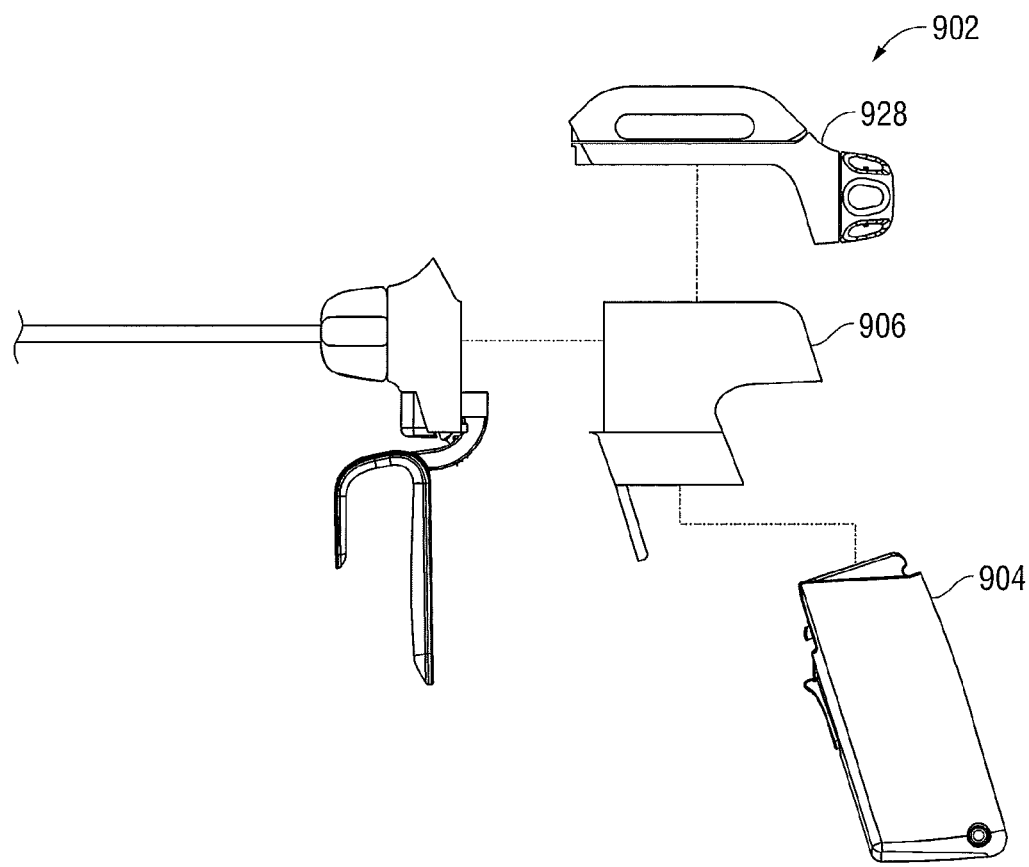
FIGS. 13A-13C are schematic views of a battery powered surgical instrument configured for use with a removable battery assembly according to still another embodiment of the present disclosure.
Figure 13B:
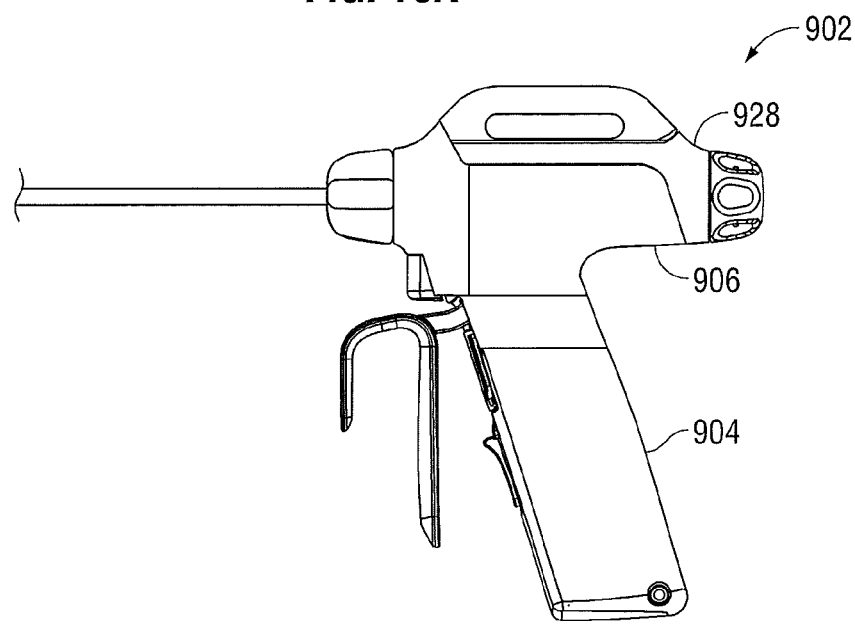
Figure 13C:
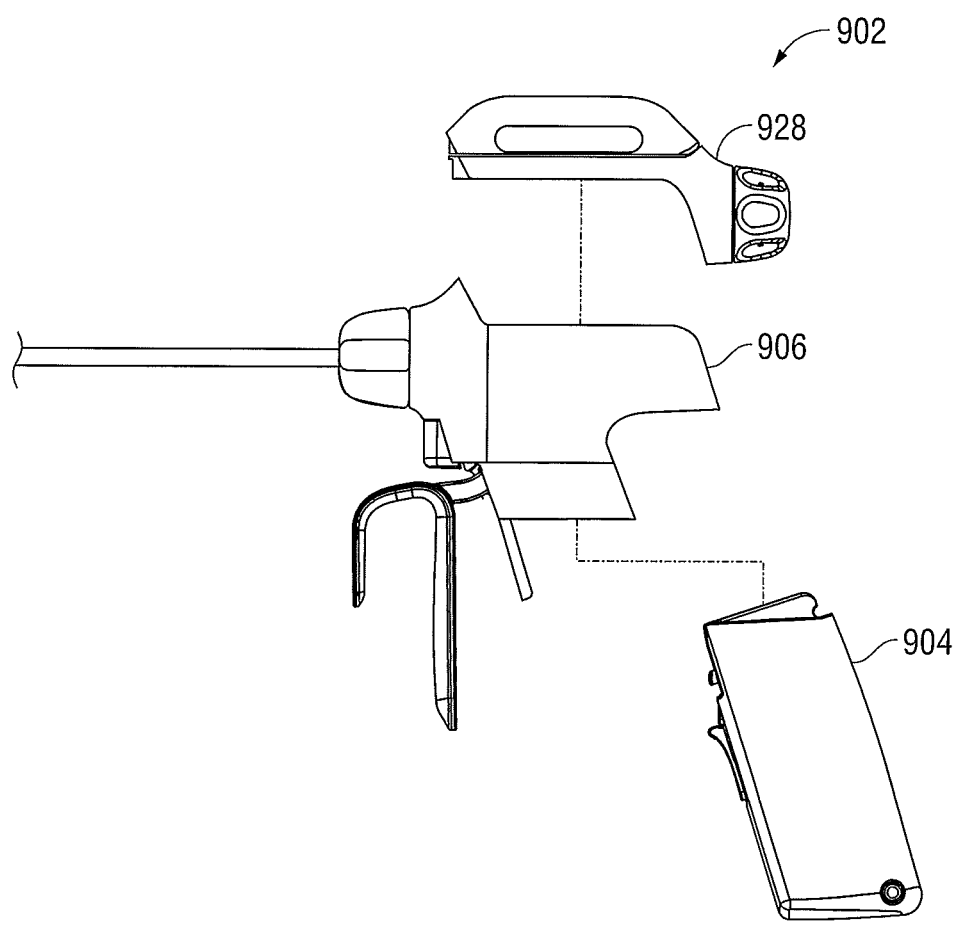

With reference to FIGS. 13A-13C, an embodiment of a portable surgical instrument is designated instrument 902. Instrument 902 is configured to releasably couple to a battery assembly 904. Instrument 902 and battery assembly 904 are substantially identical to instrument 2 and battery assembly 4 and only those features that are unique to instrument 902 and battery assembly 804 are described herein.

In the embodiment illustrated in FIGS. 13A-13C, the instrument 902 includes a selectively removable universal housing 906 that is configured to couple to the instrument 902 via one or more suitable coupling methods, e.g., snap-fit, press-fit, indent/detent configuration, etc.

Removable housing 906 is configured to couple to a generator 928 (or other suitable device) and a battery assembly 904 in a manner as described hereinbefore. The universal housing 906 is configured to accommodate various configurations of battery assemblies, as well, as various configurations of generators 928. In use, housing 906, battery assembly 904 and generator 928 may, initially, be coupled to one another, see FIG. 13A. In certain instances, once coupled to one another, a user may couple the housing 906 including the battery assembly 904 and generator 928 coupled thereto to the instrument 902, see FIG. 13B. Thereafter, the generator 928 and/or the battery assembly 904 may be uncoupled from the housing 902 in a manner as herein described before, see FIG. 13C. As can be appreciated, the unique configuration of the housing 906 allows a user to couple different generators and/or difference battery assemblies to the instrument 902. For example, in one particular embodiment, a user may couple a first generator that is configured to produce a specific tissue effect, e.g., either transect, dissect, seal and coagulate tissue, and then couple a different, second generator that is configured to produce a tissue effect that is different than the first tissue effect, e.g., either transect, dissect, seal and coagulate.

In an embodiment, the instrument 2 may be configured to electrosurgically treat tissue via RF energy. In this instance, the generator 28 is configured to generate RF energy. Moreover, the transducer and waveguide will be replaced by one or more electrical feeds that are in electrical communication with the jaw members 16, 18 and configured to provide RF energy thereto to electrosurgically treat tissue.

In yet another embodiment, the instrument 2 may be configured to staple tissue. In this instance, the generator 28 is configured to generate electrical energy and the jaw members 16, 18 will be replaced by an anvil assembly and a cartridge assembly (not explicitly shown). One or more electrical feeds that are in electrical communication with the anvil assembly and cartridge assembly are configured to provide electrical energy thereto to energize the staples in the cartridge assembly prior to ejection thereof. Alternately, the staples may be energized as they are being formed, e.g., electrical energy is applied to an anvil plate of the anvil assembly to energize the staples.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing including an elongated shaft extending distally therefrom having a longitudinal axis defined therethrough, the housing including a docking portion defining a second axis generally perpendicular to the longitudinal axis, the docking portion including at least one aperture defined therein and electrical circuitry disposed therein;
   an end effector operably supported at a distal end of the elongated shaft; and
   a battery assembly rotatable relative to the housing to selectively and pivotably engage the docking portion of the housing, the battery assembly configured to generate electrical energy, the battery assembly including at least one protrusion configured to releasably engage the at least one aperture on the docking portion and a latch mechanism slidable along the second axis and relative to the battery assembly from an initial position to latch the battery assembly to the docking portion to a subsequent position to unlatch the battery assembly from the docking portion, the battery assembly including at least one cell disposed within a cavity defined therein, the cavity defining a free space adjacent to at the least one cell configured to permit swelling of the at least one cell, wherein the battery assembly is adapted to communicate with the electrical circuitry of the docking member upon insertion of the battery assembly into the at least one aperture defined in the docking portion.

2. A surgical instrument according to claim 1, wherein a generator is configured to selectively and removably couple to the housing.

3. A surgical instrument according to claim 2, wherein the generator is configured to communicate with the battery assembly via the electrical circuitry when the generator and battery assembly are coupled to the housing.

4. A surgical instrument according to claim 1, wherein the battery assembly includes a pivot member that is configured to pivot about a corresponding member disposed on the housing of the surgical instrument.

5. A surgical instrument according to claim 4, wherein the pivot member includes a generally hook shape and is disposed at a proximal end of the battery assembly.

6. A surgical instrument according to claim 1, wherein the at least one corresponding protrusion disposed on the battery assembly is located at a distal end thereof.

7. A surgical instrument according to claim 1, wherein the at least one aperture on the docking portion is further defined by at least two apertures and the at least one protrusion on the battery assembly is further defined by at least two protrusions that are configured to engage the at least two apertures.

8. A surgical instrument according to claim 1, wherein the latch is held in a retracted position by an elongated member of the docking portion.

9. A surgical instrument e according to claim 1, wherein a top portion of the latch includes a lateral bar portion that is configured to contact the at least one protrusion on the battery assembly to prevent movement of the latch past a predetermined point.

10. A surgical instrument according to claim 1, wherein the latch includes a bottom portion that is ergonomically configured to receive a finger of a user.

11. A surgical instrument according to claim 1, wherein the battery assembly further includes an over pressure safety vent.

12. A surgical instrument according to claim 1, wherein the end effector includes a clamping jaw member, the clamping jaw member movable in relation to an active jaw member between an open position spaced from an operating surface of the active jaw member and a closed position in juxtaposed alignment with the operating surface of the active jaw member.

13. A surgical instrument according to claim 12, wherein the housing further includes a jaw lever for imparting movement of the clamping jaw.

14. A surgical instrument according to claim 1, wherein the operating surface is configured to one of transect, dissect, seal and coagulate tissue.

* * * * *